US012611152B2

(12) United States Patent
Lenga et al.

(10) Patent No.: US 12,611,152 B2
(45) Date of Patent: *Apr. 28, 2026

(54) MACHINE LEARNING IN THE FIELD OF CONTRAST-ENHANCED RADIOLOGY

(71) Applicant: Bayer Aktiengesellschaft, Leverkusen (DE)

(72) Inventors: Matthias Lenga, Leverkusen (DE); Marvin Purtorab, Hannover (DE)

(73) Assignee: Bayer Aktiengesellschaft, Leverkusen (DE)

( * ) Notice: Subject to any disclaimer, the term of this patent is extended or adjusted under 35 U.S.C. 154(b) by 61 days.

This patent is subject to a terminal disclaimer.

(21) Appl. No.: 18/280,192

(22) PCT Filed: Nov. 29, 2021

(86) PCT No.: PCT/EP2021/083321
§ 371 (c)(1),
(2) Date: Sep. 1, 2023

(87) PCT Pub. No.: WO2022/184297
PCT Pub. Date: Sep. 9, 2022

(65) Prior Publication Data
US 2024/0050053 A1    Feb. 15, 2024

(30) Foreign Application Priority Data

Mar. 2, 2021    (EP) ..................................... 21160325
Apr. 7, 2021    (EP) ..................................... 21167116

(51) Int. Cl.
*A61B 6/00*        (2006.01)
*A61B 6/03*        (2006.01)
*A61B 8/00*        (2006.01)

(52) U.S. Cl.
CPC .............. *A61B 6/481* (2013.01); *A61B 6/032* (2013.01); *A61B 8/481* (2013.01)

(58) Field of Classification Search
CPC .. A61B 6/481; G06T 2207/10116; G06T 5/60
See application file for complete search history.

(56) References Cited

U.S. PATENT DOCUMENTS

2014/0376794 A1* 12/2014 Dumoulin et al. ..... G06T 11/00
                                                                    11/3
2021/0241458 A1*  8/2021 Zaharchuk et al.
                        (Continued)

FOREIGN PATENT DOCUMENTS

WO      2018183044 A1    10/2018
WO      2018200493 A1    11/2018
                (Continued)

OTHER PUBLICATIONS

Maarten L Terpstra, "Deep learning-based image reconstruction and motion estimation from undersampled radial kspace for real-time MRI-guided radiotherapy", 2020, Phys. Med. Biol. 65, p. 1-13 (Year: 2020).*
                    (Continued)

*Primary Examiner* — Serkan Akar
*Assistant Examiner* — Kaitlyn Eunji Kim
(74) *Attorney, Agent, or Firm* — Morrison & Foerster LLP

(57)        ABSTRACT

The present invention relates to the technical field of producing artificial contrast-enhanced radiological images by way of machine learning methods.

8 Claims, 11 Drawing Sheets

(56)                 References Cited

U.S. PATENT DOCUMENTS

| | | |
|---|---|---|
| 2024/0050054 A1 | 2/2024 | Lenga et al. |
| 2024/0153163 A1 | 5/2024 | Lenga et al. |

FOREIGN PATENT DOCUMENTS

| | | |
|---|---|---|
| WO | 2019074938 A1 | 4/2019 |
| WO | 2019204406 A1 | 10/2019 |
| WO | 2019241659 A1 | 12/2019 |
| WO | 2022184298 A1 | 9/2022 |
| WO | 2022189015 A1 | 9/2022 |

OTHER PUBLICATIONS

Jan Menke, "Viewing the effective k-space coverage of MR images: phantom experiments with fast Fourier transform", 2010, Magnetic Resonance Imaging. 28, p. 1-8 (Year: 2010).*
3D Generative Adversarial Network, Learning a Probabilistic Latent Space of Object Shapes via 3D Generative-Adversarial Modeling, http://3dgan.csail.mit.edu/, 3 pages.
Abonyi, C.L. et al. (2016). "Intravascular Contrast Media in Radiography: Historical Development & Review of Risk Factors for Adverse Reactions," South American Journal of Clinical Research, vol. 3, Issue 1, 1-10.
ACR Manual on Contrast Media, 2020, ISBN: 978-1-55903-012-0.
Birkfellner, W. "Applied Medical Image Processing: A Basic Course", Verlag Taylor & Francis, 2014, Second Edition, ISBN: 9781466555570, 1-5.
Bracewell, R. (2004). "Fourier Analysis and Imaging," Verlag Springer Science & Business Media, 2004, ISBN: 9780306481871.

Burger, W. et al. (2016). Digital Image Processing An Algorithmic Introduction Using Java, Digital Image Processing, Texts in Computer Science, Second Edition, Springer-Verlag London 2016, 1-811.
Ignee, A. et al. (2016). Ultrasound contrast agents, Endosc Ultrasound. Nov.-Dec. 2016; 5(6): 355-362).
International Search Report (English translation) for PCT Application No. PCT/EP2021/083321, mailed on Mar. 14, 2022, 2 pages.
International Search Report (English translation) for PCT Application No. PCT/EP2021/083324, mailed on Mar. 15, 2022, 4 pages.
International Search Report (English translation) for PCT Application No. PCT/EP2021/083325, mailed on Mar. 11, 2022, 2 pages.
Jascinth, A. S. et al. (2016). "Contrast Agents in Computed Tomography: A Review," Journal of Applied Dental and Medical Sciences, vol. 2, Issue 2, 144-149.
Khan, S. et al. (2019). "A Guide to Convolutional Neural Networks for Computer Vision," Morgan & Claypool Publishers 2018, ISBN 1681730227, 9781681730226, 209 pages.
Lusic, H. et al. (2013). "X-Ray Computed Tomography Contrast Agents," Chem Rev. Mar. 1, 20133; 113(3), 1-64.
Nouh, M. R. et al. (2017). "Radiographic and magnetic resonances contrast agents: Essentials and tips for safe practices," World Journal of Radiology Sep. 28, 2017; 9(9): 339-349.
Perez, C. (2019). "Machine Learning Techniques: Supervised Learning and Classification. Examples with MATLAB," Amazon Digital Services LLC—Kdp Print Us, 2019, ISBN 1096996545, 9781096996545.
Robbins, J. B. (2010) "Contrast Media Tutorial," https://www.radiology.wisc.edu/wp-content/uploads/2017/10/contrast-agents-tutorial.pdf, 1-32.
Song, H.K. et al., (2000). "k-Space Weighted Image Contrast (KWIC) for Contrast Manipulation in Projection Reconstruction MRI," Magnetic Resonance in Medicine 44:825-832.

* cited by examiner

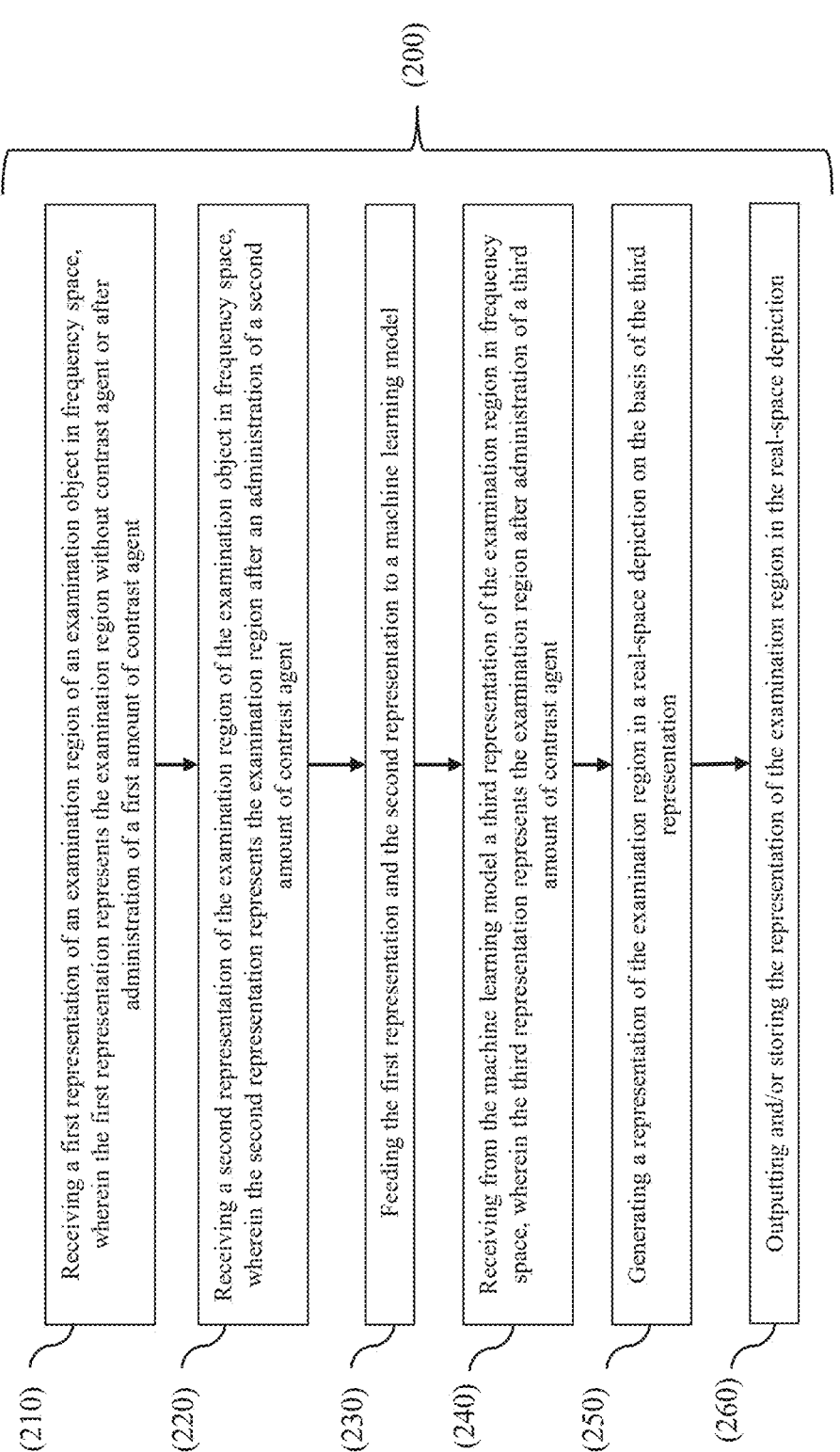

(200)

(210) Receiving a first representation of an examination region of an examination object in frequency space, wherein the first representation represents the examination region without contrast agent or after administration of a first amount of contrast agent (220) Receiving a second representation of the examination region of the examination object in frequency space, wherein the second representation represents the examination region after an administration of a second amount of contrast agent (230) Feeding the first representation and the second representation to a machine learning model (240) Receiving from the machine learning model a third representation of the examination region in frequency space, wherein the third representation represents the examination region after administration of a third amount of contrast agent (250) Generating a representation of the examination region in a real-space depiction on the basis of the third representation (260) Outputting and/or storing the representation of the examination region in the real-space depiction

Fig. 5

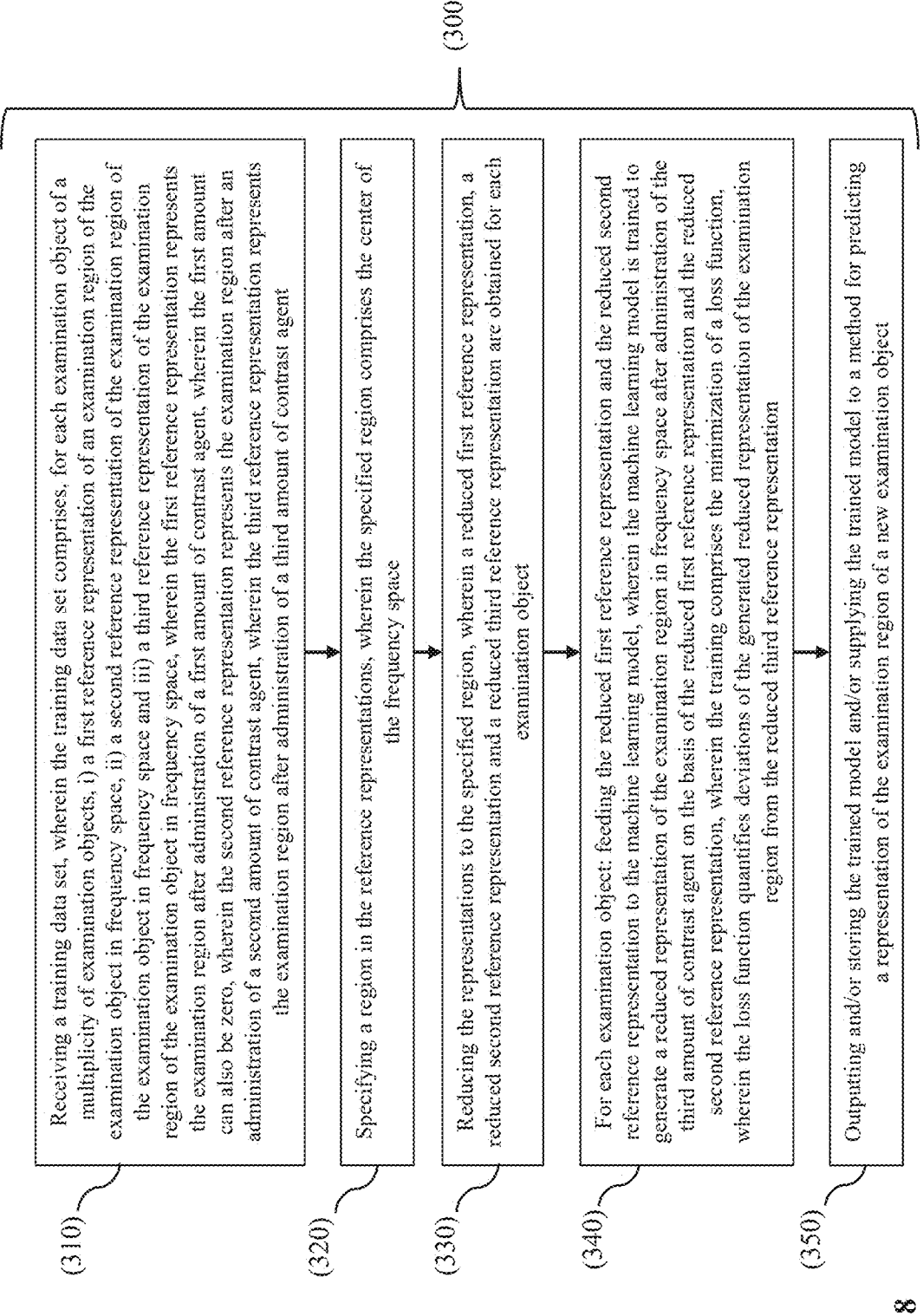

(300)

(310) Receiving a training data set, wherein the training data set comprises, for each examination object of a multiplicity of examination objects, i) a first reference representation of an examination region of the examination object in frequency space, ii) a second reference representation of the examination region of the examination object in frequency space and iii) a third reference representation of the examination region of the examination object in frequency space, wherein the first reference representation represents the examination region after administration of a first amount of contrast agent, wherein the first amount can also be zero, wherein the second reference representation represents the examination region after an administration of a second amount of contrast agent, wherein the third reference representation represents the examination region after administration of a third amount of contrast agent (320) Specifying a region in the reference representations, wherein the specified region comprises the center of the frequency space (330) Reducing the representations to the specified region, wherein a reduced first reference representation, a reduced second reference representation and a reduced third reference representation are obtained for each examination object (340) For each examination object: feeding the reduced first reference representation and the reduced second reference representation to the machine learning model, wherein the machine learning model is trained to generate a reduced representation of the examination region in frequency space after administration of the third amount of contrast agent on the basis of the reduced first reference representation and the reduced second reference representation, wherein the training comprises the minimization of a loss function, wherein the loss function quantifies deviations of the generated reduced representation of the examination region from the reduced third reference representation (350) Outputting and/or storing the trained model and/or supplying the trained model to a method for predicting a representation of the examination region of a new examination object

Fig. 8

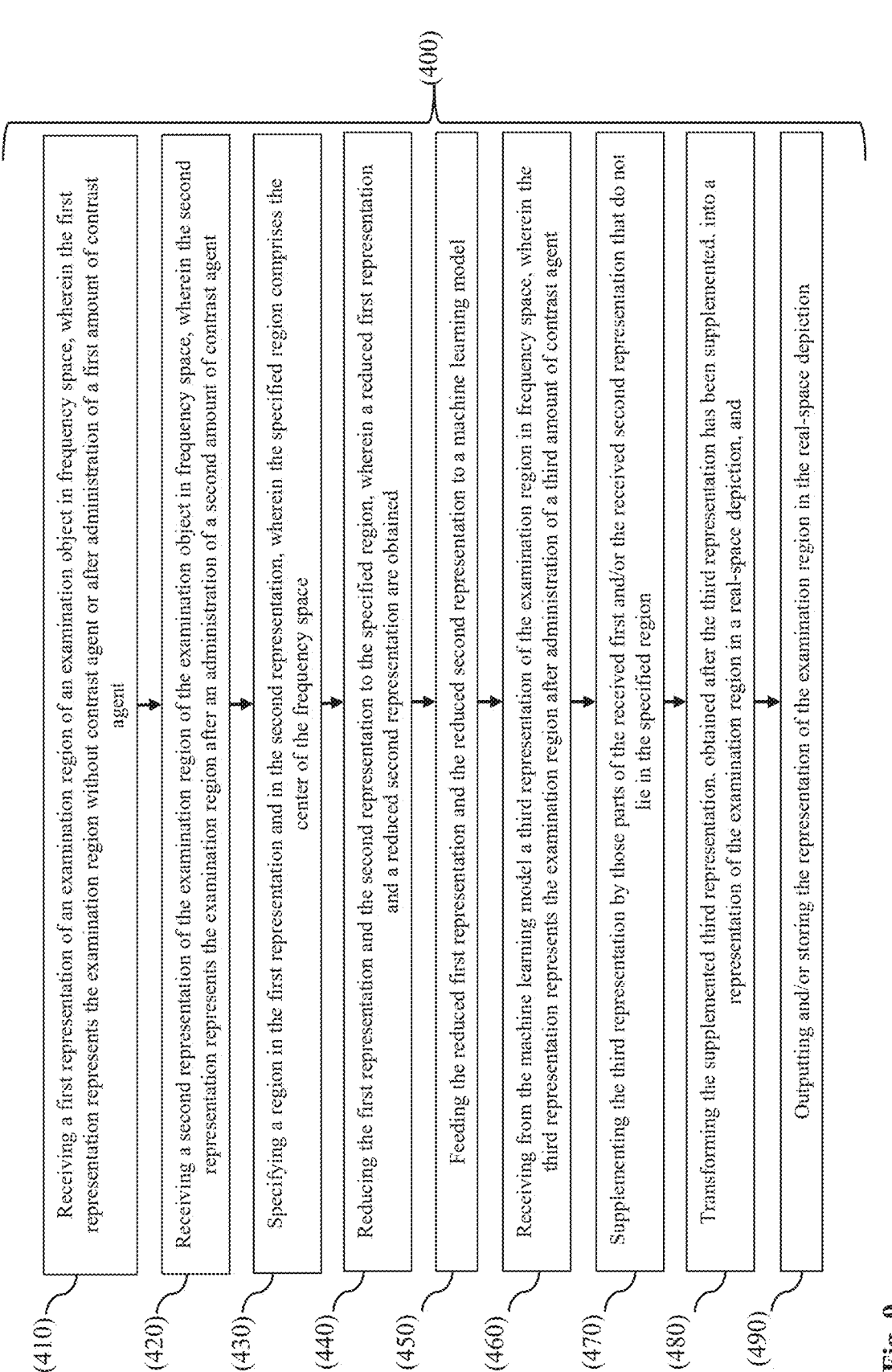

(400)

(410) Receiving a first representation of an examination region of an examination object in frequency space, wherein the first representation represents the examination region without contrast agent or after administration of a first amount of contrast agent (420) Receiving a second representation of the examination region of the examination object in frequency space, wherein the second representation represents the examination region after an administration of a second amount of contrast agent (430) Specifying a region in the first representation and in the second representation, wherein the specified region comprises the center of the frequency space (440) Reducing the first representation and the second representation to the specified region, wherein a reduced first representation and a reduced second representation are obtained (450) Feeding the reduced first representation and the reduced second representation to a machine learning model (460) Receiving from the machine learning model a third representation of the examination region in frequency space, wherein the third representation represents the examination region after administration of a third amount of contrast agent (470) Supplementing the third representation by those parts of the received first and/or the received second representation that do not lie in the specified region (480) Transforming the supplemented third representation, obtained after the third representation has been supplemented, into a representation of the examination region in a real-space depiction, and (490) Outputting and/or storing the representation of the examination region in the real-space depiction

Fig. 9

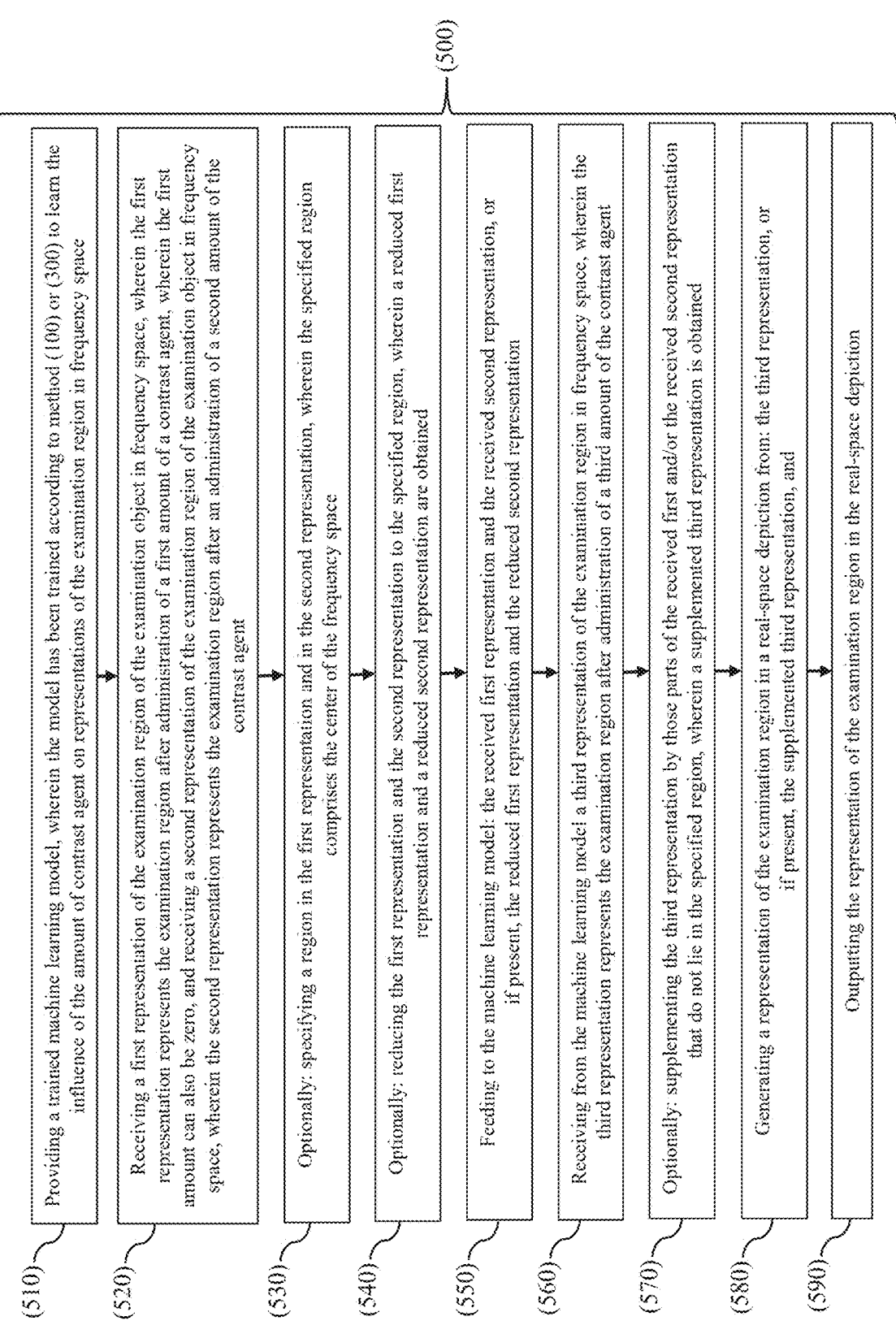

(500)

(510) Providing a trained machine learning model, wherein the model has been trained according to method (100) or (300) to learn the influence of the amount of contrast agent on representations of the examination region in frequency space (520) Receiving a first representation of the examination region of the examination object in frequency space, wherein the first representation represents the examination region after administration of a first amount of a contrast agent, wherein the first amount can also be zero, and receiving a second representation of the examination region of the examination object in frequency space, wherein the second representation represents the examination region after an administration of a second amount of the contrast agent (530) Optionally: specifying a region in the first representation and in the second representation, wherein the specified region comprises the center of the frequency space (540) Optionally: reducing the first representation and the second representation to the specified region, wherein a reduced first representation and a reduced second representation are obtained (550) Feeding to the machine learning model: the received first representation and the received second representation, or if present, the reduced first representation and the reduced second representation (560) Receiving from the machine learning model a third representation of the examination region in frequency space, wherein the third representation represents the examination region after administration of a third amount of the contrast agent (570) Optionally: supplementing the third representation by those parts of the received first and/or the received second representation that do not lie in the specified region, wherein a supplemented third representation is obtained (580) Generating a representation of the examination region in a real-space depiction from: the third representation, or if present, the supplemented third representation, and (590) Outputting the representation of the examination region in the real-space depiction

Fig. 10

MACHINE LEARNING IN THE FIELD OF CONTRAST-ENHANCED RADIOLOGY

CROSS REFERENCE TO RELATED APPLICATIONS

This application is a national stage application under 35 U.S.C. § 371 of International Application No. PCT/EP2021/083321, filed internationally on Nov. 29, 2021, which claims priority to European Application No. 21160325.3, filed on Mar. 2, 2021, and European Application No. 21167116.9, filed on Apr. 7, 2021, the entire content of each is hereby incorporated by reference in their entirety.

FIELD

The present invention is directed to the generation of artificial contrast-enhanced radiological images using machine learning methods.

BACKGROUND

WO2019/074938A1 discloses a method for reducing the amount of contrast agent in the generation of radiological images with the aid of an artificial neural network.

In a first step, a training data set is generated. For a multiplicity of persons, the training data set comprises for each person i) a native radiological image (zero-contrast image), ii) a radiological image after the administration of a low amount of contrast agent (low-contrast image) and iii) a radiological image after the administration of a standard amount of contrast agent (full-contrast image). The term "multiplicity" preferably means more than 10, even more preferably more than 100.

In a second step, an artificial neural network is trained to predict for each person of the training data set, based on the native image and the image after administration of a low amount of contrast agent, an artificial radiological image which shows an acquisition region after the administration of the standard amount of contrast agent. The measured radiological image after the administration of a standard amount of contrast agent is used in each case as reference (ground truth) in the training.

In a third step, the trained artificial neural network can be used to predict for a new person, based on a native image and a radiological image after the administration of a low amount of contrast agent, an artificial radiological image which shows the acquired region as it would look if a standard amount of contrast agent had been administered.

The method disclosed in WO2019/074938A1 has disadvantages.

First, the method disclosed in WO2019/074938A1 co-registration of the radiological images in order to match the individual radiological images such that the pixels/voxels correspond with one another, i.e., so that one pixel/voxel of a radiological image from one person shows the same examination region as the pixel/voxel of a different radiological image from said person. If the radiological images do not correspond, artefacts that can cover and/or distort and/or simulate small anatomical structures in the acquisition region may appear in the artificially generated radiological images.

Furthermore, the method disclosed in WO2019/074938A1 always uses complete radiological images for prediction. When the training of the artificial neural network and the prediction of an artificial radiological image involve the use of radiological images in addition to those mentioned above under numerals i) and ii)—e.g., radiological images after administration of varying amounts of contrast agent—the calculation complexity for generation of the artificial radiological image can rapidly become very great. Large amounts of time may be required to calculate artificial radiological images. In order to carry out calculations within an appropriate time span, special and/or expensive hardware may be required. While radiological images may be reduced to partial regions (patches) and processed separately from one another in order to prevent overloading of the memory of the computer with overly large radiological images, such an approach can lead to artefacts at the interfaces when the partial regions processed separately from one another are re-joined to form a complete radiological image (i.e., stitching artefacts). The subsequent removal of such stitching artefacts adds complexity and increases the risk of errors in the synthetically generated radiological images that could be misinterpreted by a radiologist (e.g., increases the risk of misdiagnosis).

SUMMARY

The object of the present invention is to produce a solution for generating artificial radiological images that is tolerant with respect to errors in co-registration, in which the prediction requires less computing power, in which the calculation complexity can be matched to the given hardware and/or the time available, and in which the risk of artefacts (especially stitching artefacts) can be reduced.

This object is achieved by the subjects of the independent claims. Preferred embodiments of the present invention are found in the dependent claims, in the present description and in the drawings.

The present disclosure provides a computer-implemented method comprising:

receiving a first representation of an examination region of an examination object in frequency space, wherein the first representation represents the examination region without contrast agent or after administration of a first amount of contrast agent, receiving a second representation of the examination region of the examination object in frequency space, wherein the second representation represents the examination region after an administration of a second amount of contrast agent, feeding at least part of the first representation and at least part of the second representation to a machine learning model, receiving from the machine learning model a third representation of the examination region in frequency space, wherein the third representation represents the examination region after administration of a third amount of contrast agent, generating a representation of the examination region in a real-space depiction on the basis of the third representation, and outputting and/or storing the representation of the examination region in the real-space depiction.

The present disclosure further provides a computer system comprising:

a receiving unit, a control and calculation unit, and an output unit, wherein the control and calculation unit is configured to prompt the receiving unit to receive at least two representations of an examination region of an examination object, a first representation and a second representation, wherein the first representation represents the examination region without contrast agent or after administration of a first amount of contrast agent, wherein the second representation represents the examination region after an adminis- tration of a second amount of contrast agent, wherein the control and calculation unit is configured to feed at least part of the first representation and at least part of the second representation to a machine learning model, wherein the control and calculation unit is configured to receive from the machine learning model a third representation of the examination region, wherein the third representation represents the examination region in frequency space after administration of a third amount of contrast agent, wherein the control and calculation unit is configured to generate on the basis of the third representation a representation of the examination region in real space, and wherein the control and calculation unit is configured to prompt the output unit to output and/or store the representation of the examination region in real space.

The present disclosure further provides a non-transitory computer readable storage medium storing instructions that, when executed by one or more processors of a computer system, cause the computer system to:

receive a first representation of an examination region of an examination object in frequency space, wherein the first representation represents the examination region without contrast agent or after administration of a first amount of contrast agent, receive a second representation of the examination region of the examination object in frequency space, wherein the second representation represents the examination region after an administration of a second amount of contrast agent, feed at least part of the first representation and at least part of the second representation to a machine learning model, receive from the machine learning model a third representation of the examination region in frequency space, wherein the third representation represents the examination region after administration of a third amount of contrast agent, generate a representation of the examination region in a real-space depiction on the basis of the third representation, and output and/or store the representation of the examination region in the real-space depiction.

The present disclosure further provides for the use of a contrast agent in a radiological method, the radiological method comprising:

generating a first representation of an examination region of an examination object in frequency space, wherein the first representation represents the examination region without the contrast agent or after administration of a first amount of the contrast agent, generating a second representation of the examination region of the examination object in frequency space, wherein the second representation represents the examination region after an administration of a second amount of the contrast agent, wherein the second amount differs from the first amount, feeding at least part of the first representation and at least part of the second representation to a machine learning model, receiving from the machine learning model a third representation of the examination region in frequency space, wherein the third representation represents the examination region after administration of a third amount of the contrast agent, wherein the third amount differs from the first amount and from the second amount, generating a representation of the examination region in a real-space depiction on the basis of the third representation, and outputting and/or storing the representation of the examination region in the real-space depiction.

Further provided is a contrast agent for use in a radiological method, the method comprising:

generating a first representation of an examination region of the examination object in frequency space, wherein the first representation represents the examination region without the contrast agent or after administration of a first amount of the contrast agent, generating a second representation of the examination region of the examination object in frequency space, wherein the second representation represents the examination region after administration of the second amount of the contrast agent, feeding at least part of the first representation and at least part of the second representation to a machine learning model, receiving from the machine learning model a third representation of the examination region in frequency space, wherein the third representation represents the examination region after administration of a third amount of the contrast agent, wherein the third amount of contrast agent differs from the first amount and from the second amount, generating a representation of the examination region in a real-space depiction on the basis of the third representation, and outputting and/or storing the representation of the examination region in the real-space depiction.

Further provided is a kit comprising a contrast agent and a computer program according to the invention.

BRIEF DESCRIPTION OF THE FIGURES

The invention will now be described, by way of example only, with reference to the following figures.

FIG. 5 shows a method for predicting a representation of an examination region of an examination object, according to some embodiments.

5

FIG. 8 shows another method for training a machine learning model, according to some embodiments.

FIG. 9 shows another method for predicting a representation of an examination region of an examination object, according to some embodiments.

FIG. 10 shows another method, for predicting a representation of an examination region of an examination object, according to some embodiments.

Figure 11:
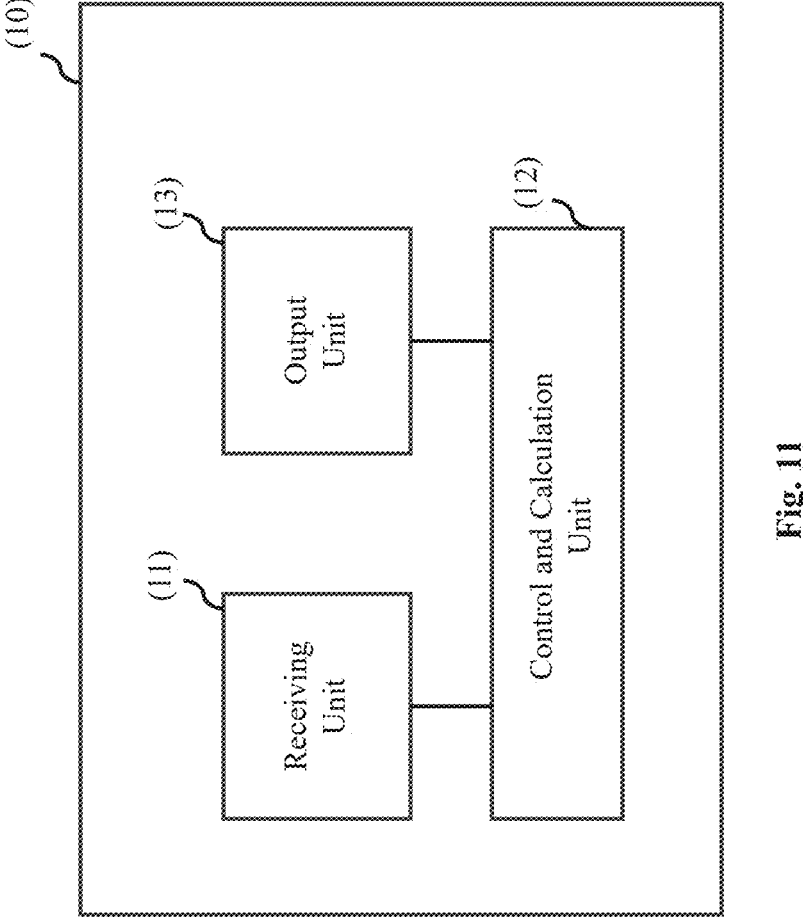

FIG. 11 shows a computer system, according to some embodiments.

DETAILED DESCRIPTION

The invention will be more particularly elucidated below without distinguishing between the subjects of the invention (method, computer system, computer program, use, contrast agent for use, kit). On the contrary, the following elucidations are intended to apply analogously to all the subjects of the invention, irrespective of in which context (method, computer system, computer program, use, contrast agent for use, kit) they occur.

Where steps are stated in an order in the present description or in the claims, this does not necessarily mean that the invention is limited to the order stated. Instead, it is conceivable that the steps are also executed in a different order or else in parallel with one another, unless one step builds on another step, which absolutely requires that the step building on the previous step be executed subsequently (which will however become clear in the individual case). The orders stated are thus preferred embodiments of the invention.

With the aid of the present invention, it is possible to generate an artificial radiological image of an examination region of an examination object.

The "examination object" is usually a living being, preferably a mammal, very particularly preferably a human.

The "examination region" is part of the examination object, for example an organ or part of an organ.

The examination region, also called image volume (field of view, FOV), is in particular a volume which is imaged in radiological images. The examination region is typically defined by a radiologist, for example on an overview image (localizer). It is of course also possible for the examination region to alternatively or additionally be defined automatically, for example on the basis of a selected protocol.

The examination region is subjected to a radiological examination.

"Radiology" is the branch of medicine that deals with the application of electromagnetic rays and mechanical waves (including for instance ultrasound diagnostics) for diagnostic, therapeutic and/or scientific purposes. Besides X-rays, other ionizing radiation such as gamma radiation or electrons are also used. Since a fundamental intended purpose is imaging, radiology also includes other imaging methods such as sonography and magnetic resonance imaging (nuclear magnetic resonance imaging), even though these methods do not use ionizing radiation. The term "radiology" in the context of the present invention thus encompasses in particular the following examination methods: computed tomography, magnetic resonance imaging, sonography.

In a preferred embodiment of the present invention, the radiological examination is a magnetic resonance imaging examination.

Magnetic resonance imaging (MRI), is an imaging method which is used especially in medical diagnostics for depicting structure and function of the tissues and organs in the human or animal body.

In MRI, the magnetic moments of protons in an examination object are aligned in a basic magnetic field, resulting in a macroscopic magnetization along a longitudinal direction that is then deflected from the resting position by irradiation with high-frequency (HF) pulses (excitation). The return of the excited states to the resting position (relaxation), or magnetization dynamics, is then detected as relaxation signals using one or more HF receiver coils.

For spatial encoding, rapidly switched magnetic gradient fields are superimposed on the basic magnetic field. The captured relaxation signals, or detected MRI data, are initially present as raw data in a frequency space and can be transformed by subsequent inverse Fourier transform into real space (image space).

In the case of native MRI, the tissue contrasts are created by the different relaxation times (T1 and T2) and the proton density. T1 relaxation describes the transition of the longitudinal magnetization to its equilibrium state. T1, also known as longitudinal relaxation time or spin-lattice relaxation time, is the time taken to reach 63.21% of the equilibrium magnetization prior to the resonance excitation. T2 relaxation describes in an analogous manner the transition of transverse magnetization to its equilibrium state.

In radiological examinations, contrast agents are commonly used for contrast enhancement.

"Contrast agents" are substances or mixtures of substances which improve the depiction of structures and functions of the body in imaging methods such as X-ray diagnostics, magnetic resonance imaging and sonography.

In computed tomography, iodine-containing solutions are usually used as contrast agents. In magnetic resonance imaging (MRI), superparamagnetic substances (e.g., iron oxide nanoparticles, superparamagnetic iron-platinum particles (SIPPs)) or paramagnetic substances (e.g., gadolinium chelates, manganese chelates) are usually used as contrast agents. In the case of sonography, liquids containing gas-filled microbubbles are usually administered intravenously. Examples of contrast agents can be found in the literature (see, for example, A. S. L. Jascinth et al.: *Contrast Agents in computed tomography: A Review*, Journal of Applied Dental and Medical Sciences, 2016, Vol. 2, Issue 2, 143-149; H. Lusic et al.: *X-ray-Computed Tomography Contrast Agents*, Chem. Rev. 2013, 113, 3, 1641-1666; https://www.radiology.wisc.edu/wp-content/uploads/2017/10/contrast-agents-tutorial.pdf, M. R. Nough et al.: *Radiographic and magnetic resonances contrast agents: Essentials and tips for safe practices*, World J Radiol. 2017 Sep. 28; 9(9): 339-349; L. C. Abonyi et al.: *Intravascular Contrast Media in Radiography: Historical Development & Review of Risk Factors for Adverse Reactions*, South American Journal of Clinical Research, 2016, Vol. 3, Issue 1, 1-10; ACR Manual on Contrast Media, 2020, ISBN: 978-1-55903-012-0; A. Ignee et al.: *Ultrasound contrast agents*, Endosc Ultrasound. 2016 November-December; 5(6): 355-362).

MRI contrast agents exert their effect by altering the relaxation times of structures that take up contrast agents. A distinction can be made between two groups of substances: paramagnetic and superparamagnetic substances. Both groups of substances have unpaired electrons that induce a magnetic field around the individual atoms or molecules. Superparamagnetic contrast agents result in a predominant shortening of T2, whereas paramagnetic contrast agents mainly lead to a shortening of T1. The effect of said contrast agents is indirect, since the contrast agent itself does not emit a signal, but instead merely influences the intensity of signals in its vicinity. An example of a superparamagnetic contrast agent is iron oxide nanoparticles (SPIO, superparamagnetic iron oxide). Examples of paramagnetic contrast agents are gadolinium chelates such as gadopentetate dime-glumine (trade name: Magnevist® and others), gadoteric acid (Dotarem®, Dotagita®, Cyclolux®), gadodiamide (Omniscan®), gadoteridol (ProHance®) and gadobutrol (Gadovist®).

With the aid of the present invention, it is possible to generate an artificial radiological image which shows the examination region of an examination object as it would look if a specific amount of contrast agent had been administered to the examination object/examination region without said specific amount actually having to be administered.

To this end, use is made of a machine learning model (also referred to as prediction model in this description) which learns, based on training data, how different amounts of contrast agent affect the contrast of a radiological image of an examination region. The trained model can then be used to predict a radiological image having a contrast enhancement which would arise after administration of a specific amount of contrast agent without said amount actually having to be administered.

Similar to WO2019/074938A1, the present invention can, for example, be used to reduce the amount of administered contrast agent without having to dispense with the advantages of a high dose of contrast agent (i.e., high contrast enhancement).

However, in the invention provided herein, radiological images are not predicted on the basis of images, as described in WO2019/074938A1. The images used in WO2019/074938A1 for prediction of artificial radiological images are representations (depictions) of an examination region in real space (also called image space).

According to the invention, the machine learning model is trained with the aid of representations of an examination region of a multiplicity of examination objects in frequency space. The prediction is done based on representations of the examination region in frequency space (also referred to as spatial frequency space or Fourier space or frequency domain or Fourier depiction).

In magnetic resonance imaging, the raw data usually arise as so-called k-space data owing to the above-described measurement method. Said k-space data are a depiction of an examination region in a frequency space. Such k-space data can be used for training of a machine learning model, for validation of the model, and for prediction with the aid of the trained model according to the present invention.

If, however, representations are present in real space, they can, for example, be converted (transformed) by means of Fourier transform into a representation in frequency space.

Thus, if a radiological image of an examination region is present in the form of a two- or three-dimensional image in real space, this representation of the examination region can, for example, be converted by a 2D or 3D Fourier transform into a two- or three-dimensional representation of the examination region in frequency space.

Conversely, representations in frequency space can be converted (transformed) by inverse Fourier transform into a representation in real space.

Figure 1:
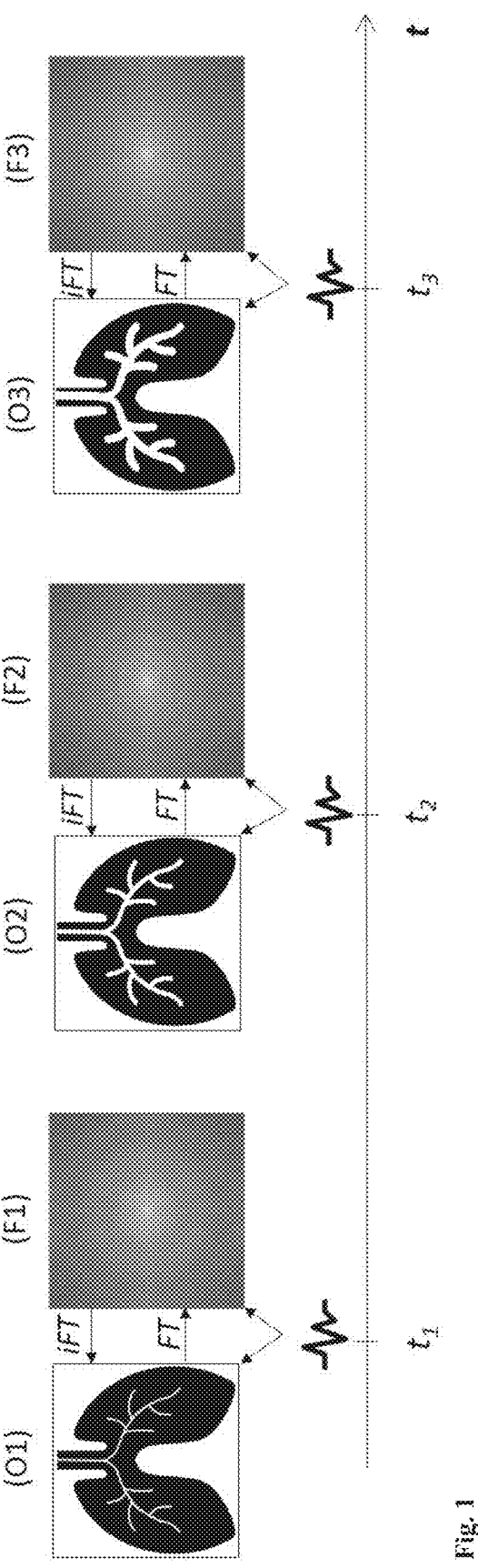
FIG. 1 shows a connection between representations of an examination region in real space and in frequency space, according to some embodiments.

FIG. 1 shows schematically and exemplarily the connection between representations of an examination region in real space and in frequency space. Specifically, FIG. 1 depicts a timeline. At three different time points $t_1$, $t_2$, and $t_3$, representations of an examination region are generated on the basis of measurement. The examination region is the lung of a human. At time point $t_1$, is a first representation is generated. This can be a representation O1 of the examination region (the lung) in real space or a representation F1 of the examination region (the lung) in frequency space. The representation O1 of the examination region in real space can be converted by means of Fourier transform (FT) into a representation F1 of the examination region in frequency space. The representation F1 of the examination region in frequency space can be converted by means of inverse Fourier transform (iFT) into a representation O1 of the examination region in real space.

The representations O1 and F1 can, for example, be representations of the examination region without a contrast agent or after administration of a first amount of contrast agent.

The two representations O1 and F1 comprise the same information about the examination region, just in a different depiction.

At time point $t_2$, a further representation is generated. This can be a representation O2 of the examination region (the lung) in real space or a representation F2 of the examination region (the lung) in frequency space. The representation O2 of the examination region in real space can be converted by means of Fourier transform (FT) into a representation F2 of the examination region in frequency space. The representation F2 of the examination region in frequency space can be converted by means of inverse Fourier transform (iFT) into a representation O2 of the examination region in real space.

The representations O2 and F2 can, for example, be representations of the examination region after administration of a second amount of contrast agent.

The two representations O2 and F2 comprise the same information about the examination region, just in a different depiction.

At time point $t_3$, a further representation is generated. This can be a representation O3 of the examination region (the lung) in real space or a representation F3 of the examination region (the lung) in frequency space. The representation O3 of the examination region in real space can be converted by means of Fourier transform (FT) into a representation F3 of the examination region in frequency space. The representation F3 of the examination region in frequency space can be converted by means of inverse Fourier transform (iFT) into a representation O3 of the examination region in real space.

The representations O3 and F3 can, for example, be representations of the examination region after administration of a third amount of contrast agent.

The two representations O3 and F3 comprise the same information about the examination region, just in a different depiction.

The representations O1, O2 and O3 of the examination region in real space are the familiar representations for humans; such real-space depictions can be immediately grasped by humans. The representations O1, O2 and O3 show what influence different amounts of contrast agent can have on the appearance of the examination region in an MRI examination. In the present case, the amount of contrast agent rises from O1 via O2 to O3. The same information is also contained in the representations F1, F2 and F3; however, said information is more difficult to grasp for humans from the depictions F1, F2 and F3.

It is also conceivable to use a transform other than the Fourier transform in order to convert real-space representations into frequency-space representations. The three main properties which must be satisfied by such a transform are:
  a) existence of a clear inverse transform (clear connection between real-space depiction and frequency-space depiction),
  b) locality of the contrast information, and
  c) robustness with respect to deficient image registration.

Details on transformation from one depiction into another are described in a multitude of textbooks and publications (see, for example: W. Burger, M. J. Burge: *Digital Image Processing: An Algorithmic Introduction Using Java*, Texts in Computer Science, 2nd edition, Springer-Verlag, 2016, ISBN: 9781447166849; W. Birkfellner: *Applied Medical Image Processing, Second Edition: A Basic Course*, Verlag Taylor & Francis, 2014, ISBN: 9781466555570; R. Bracewell: *Fourier Analysis and Imaging*, Verlag Springer Science & Business Media, 2004, ISBN: 9780306481871).

In order for the machine learning model (prediction model) according to the invention to be able to make the predictions described here, it must be appropriately configured (trained).

Here, the term "prediction" means that at least one representation of an examination region that represents the examination region after an administration of a specific amount of contrast agent in frequency space is calculated on the basis of at least two representations of the examination region in frequency space, wherein the at least two representations represent the examination region after administration of different amounts of contrast agent and/or after administration of different contrast agents.

In other words: at least one first representation of an examination region of an examination object and at least one second representation of the examination region of the examination object are used in order to predict at least one third representation of the examination region of the examination object. All the representations, the at least one first, the at least one second and the at least one third representation, are representations of the examination region in frequency space.

The at least one first representation represents the examination region after administration of a first amount of a first contrast agent, it being possible for said first amount to also be zero (no administration of a contrast agent).

The at least one second representation represents the examination region after administration of a second amount of the first contrast agent or a second amount of a second contrast agent. If the first contrast agent is used to generate the second representation, the second amount is usually not equal to the first amount. If a second contrast agent is used, the second amount may be equal to or not equal to the first amount.

The at least one third representation represents the examination region after administration of a third amount of the first contrast agent or a third amount of the second contrast agent or a third amount of a third contrast agent. If the same contrast agent is used to generate the first representation, the second representation and the third representation, the third amount is usually not equal to the second amount and not equal to the first amount; the following preferably applies to the first amount M1, the second amount M2 and the third amount M3: the first amount M1 is greater than or equal to zero, the second amount M2 is greater than the first amount M1, and the third amount M3 is greater than the second amount M2 ($0 \leq M1 < M2 < M3$).

If the generation of the third representation involves the use of a different contrast agent compared to the generation of the first and/or the second representation, the amount of the different contrast agent may be equal to or not equal to the amount(s) of the contrast agent(s) for the generation of the first and/or the second representation.

The prediction model can thus be trained to learn the influence of different amounts of contrast agent on representations of the examination region in frequency space; however, it can also be trained to learn the influence of different contrast agents on representations of the examination region in frequency space.

The prediction model is preferably created (configured, trained) with the aid of a self-learning algorithm in a supervised machine learning process. Training data are used for learning. Said training data comprise, of a multiplicity of examination objects, a plurality of representations of an examination region for each examination object. The examination region is usually the same for all examination objects (e.g., part of a human body or an organ or part of an organ). The representations of the training data set are also referred to as reference representations in this description.

For each examination object, the training data comprise i) at least one first reference representation of the examination region in frequency space that represents the examination region without contrast agent or after administration of a first amount of contrast agent, ii) at least one second reference representation of the examination region in frequency space that represents the examination region after administration of a second amount of contrast agent, and iii) at least one third reference representation of the examination region in frequency space that represents the examination region after administration of a third amount of contrast agent. The following applies, as described above: the first, second and third amounts of contrast agent and/or the particular contrast agents used differ from one another.

The prediction model is trained to predict (calculate) for each examination object the at least one third reference representation on the basis of the at least one first reference representation and the at least one second reference representation.

The self-learning algorithm generates, during machine learning, a statistical model which is based on the training data. This means that the examples are not simply learnt by heart, but that the algorithm "recognizes" patterns and regularities in the training data. The prediction model can thus also assess unknown data. Validation data can be used to test the quality of the assessment of unknown data.

The prediction model can be trained by means of supervised learning, i.e., triples of data sets (first, second and third representations) are presented in succession to the algorithm. The algorithm then learns a relationship between these data sets.

Self-learning systems trained by means of supervised learning are widely described in the prior art (see, for example, C. Perez: *Machine Learning Techniques: Supervised Learning and Classification*, Amazon Digital Services LLC—Kdp Print Us, 2019, ISBN 1096996545, 9781096996545).

Preferably, the prediction model is an artificial neural network or comprises such a network.

An artificial neural network comprises at least three layers of processing elements: a first layer with input neurons (nodes), an N-th layer with at least one output neuron (nodes) and N−2 inner layers, where N is a natural number and greater than 2.

The input neurons serve to receive first and second representations. The output neurons serve to output at least one third representation for at least one first representation and at least one second representation.

The processing elements of the layers between the input neurons and the output neurons are connected to one another in a predetermined pattern with predetermined connection weights.

Preferably, the artificial neural network is a convolutional neural network (CNN).

A convolutional neural network is capable of processing input data in the form of a matrix. A CNN consists essentially of filters (convolutional layer) and aggregation layers (pooling layer) which are repeated alternately and, at the end, of one layer or multiple layers of "normal" completely connected neurons (dense/fully connected layer).

The training of the neural network can, for example, be carried out using a backpropagation method. The aim here in respect of the network is maximum reliability of mapping of given input data onto given output data. The mapping quality is described by a loss function. The goal is to minimize the loss function. In the case of the backpropagation method, an artificial neural network is taught by the alteration of the connection weights.

In the trained state, the connection weights between the processing elements contain information regarding the relationship between, firstly, the at least one first representation and the at least one second representation and, secondly, the at least one third representation. Said information can be used in order to predict at least one third representation on the basis of at least one first and at least one second representation.

A cross-validation method can be used in order to divide the data into training and validation data sets. The training data set is used in the backpropagation training of network weights. The validation data set is used in order to check the accuracy of prediction with which the trained network can be applied to unknown data.

Further details on the construction and training of artificial neural networks can be gathered from the prior art (see, for example: S. Khan et al.: *A Guide to Convolutional Neural Networks for Computer Vision*, Morgan & Claypool Publishers 2018, ISBN 1681730227, 9781681730226, WO2018/183044A1, WO2018/200493, WO2019/074938A1, WO2019/204406A1, WO2019/241659A1).

Preferably, the prediction model is a generative adversarial network (GAN) (see, for example: http://3dgan.csail.mit.edu/).

In addition to the representations, further information about the examination object, about the examination region, about examination conditions, and/or about the radiological examination methods can also be used for training, validation and prediction.

Examples of information about the examination object are: sex, age, weight, height, anamnesis, nature and duration and amount of medicaments already ingested, blood pressure, central venous pressure, breathing rate, serum albumin, total bilirubin, blood sugar, iron content, breathing capacity, and the like. Said information about the examination object can, for example, be read from a database or an electronic patient file.

Examples of information about the examination region are: pre-existing conditions, operations, partial resection, liver transplantation, iron liver, fatty liver, and the like.

Figure 2:
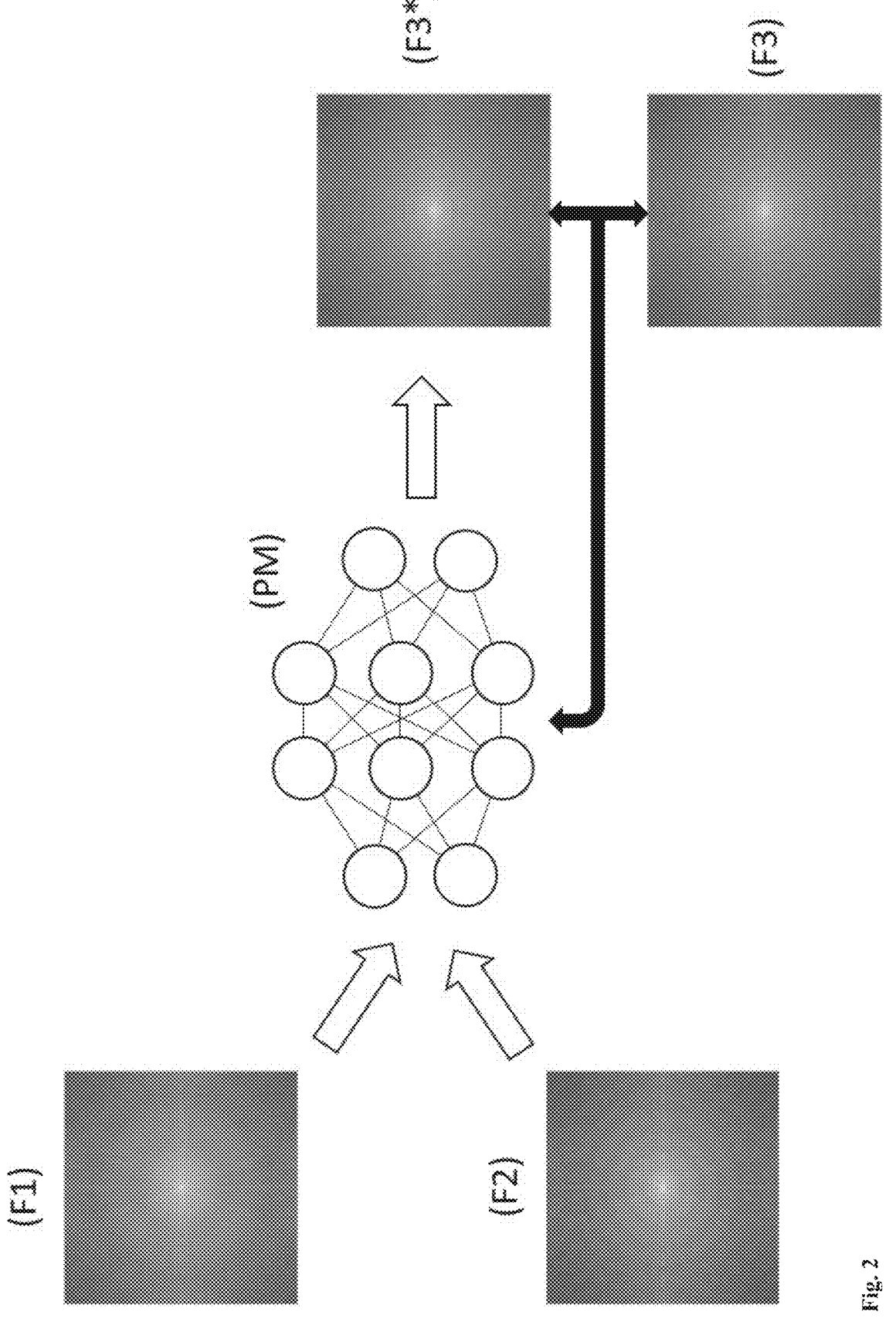
FIG. 2 shows how the representations (F1), (F2) and (F3) of the examination region in frequency space shown in FIG. 1 can be used for training a prediction model (PM), according to some embodiments.

FIG. 2 shows schematically and exemplarily how the representations (F1), (F2), and (F3) of the examination region in frequency space as generated in FIG. 1 can be used for training a prediction model (PM). The representations (F1), (F2), and (F3) form a set of training data of an examination object. The training is done using a multiplicity of training data sets of a multiplicity of examination objects.

The representations (F1) and (F2) are a first and a second representation of an examination region in frequency space. These representations represent the examination region after the administration of different amounts of contrast agent (it is possible that, in one case, no contrast agent has been administered).

The representation (F3) is a third representation of the examination region in frequency space that represents the examination region after the administration of a third amount of contrast agent.

In FIG. 2, the prediction model is trained to predict the representation (F3) of the examination region in frequency space from the representations (F1) and (F2) of the examination region in frequency space.

The representations (F1) and (F2) are input into the prediction model (PM) and the prediction model calculates a representation (F3*) from the representations (F1) and (F2). The asterisk (*) signals that the representation (F3*) is a predicted representation. The calculated representation (F3*) is compared with the representation (F3). The deviations between the calculated representation (F3*) and the measured representation (F3) can be used in a backpropagation method to train the prediction model to reduce the deviations to a defined minimum. If the prediction model has been trained on the basis of a multiplicity of training data sets of a multiplicity of examination objects and if the prediction has reached a defined accuracy, the trained prediction model can be used for prediction.

Figure 3:
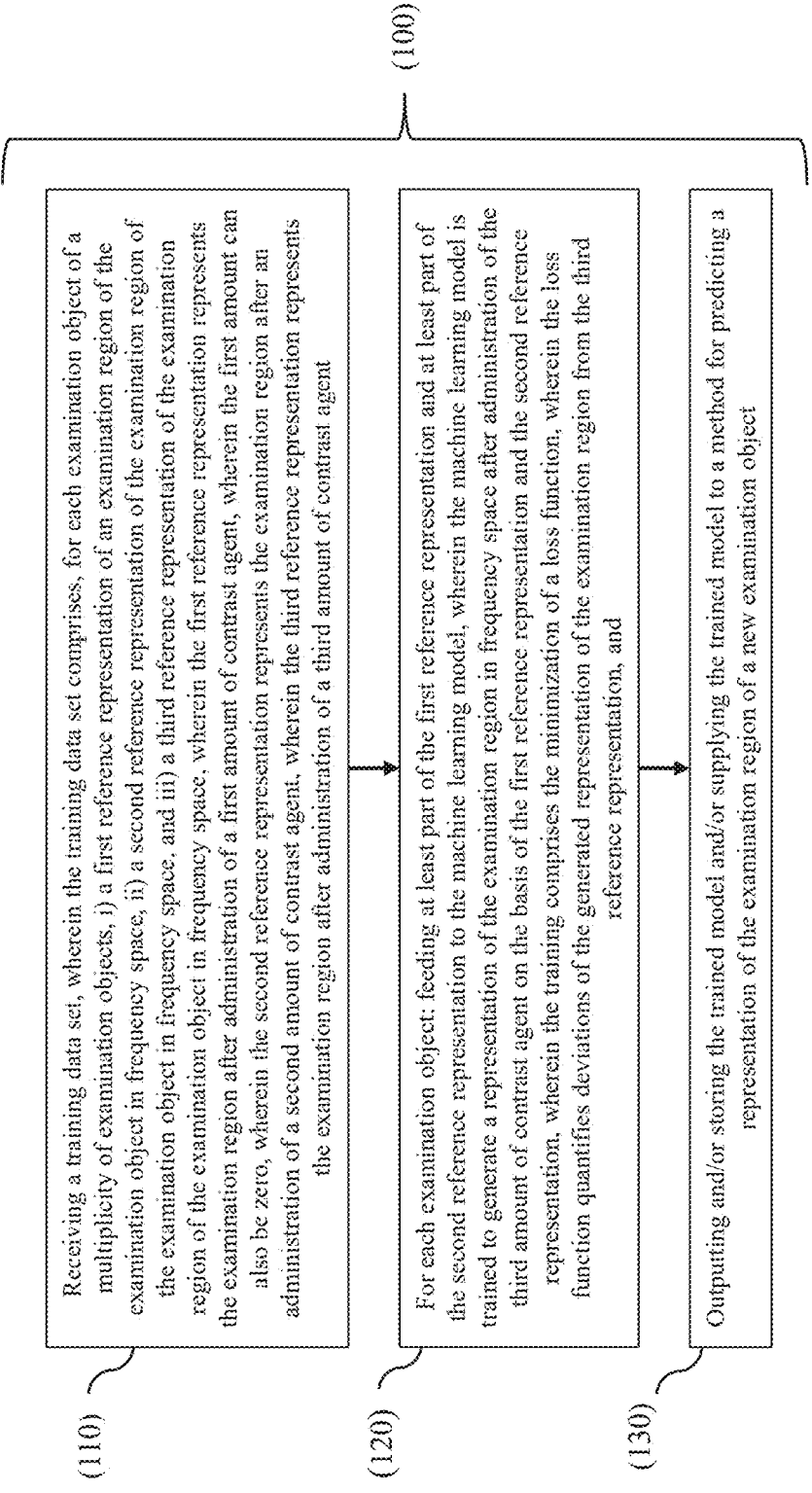
FIG. 3 shows a method for training a machine learning model, according to some embodiments.

FIG. 3 shows exemplarily and schematically in the form of a flow chart a preferred embodiment of the method according to the invention for training a machine learning model.

The method (100) comprises the following steps:

(110) receiving a training data set, wherein the training data set comprises, for each examination object of a multiplicity of examination objects, i) a first reference representation of an examination region of the examination object in frequency space, ii) a second reference representation of the examination region of the examination object in frequency space, and iii) a third reference representation of the examination region of the examination object in frequency space, wherein the first reference representation represents the examination region after administration of a first amount of contrast agent, wherein the first amount can also be zero, wherein the second reference representation represents the examination region after an administration of a second amount of contrast agent, wherein the third reference representation represents the examination region after administration of a third amount of contrast agent, (120) for each examination object: feeding at least part of the first reference representation and at least part of the second reference representation to the machine learning model, wherein the machine learning model is trained to generate a representation of the examination region in frequency space after administration of the third amount of contrast agent on the basis of the first reference representation and the second reference representation, wherein the training comprises the minimization of a loss function, wherein the loss function quantifies deviations of the generated representation of the examination region from the third reference representation, and (130) outputting and/or storing the trained model and/or supplying the trained model to a method for predicting a representation of the examination region of a new examination object.

Figure 4:
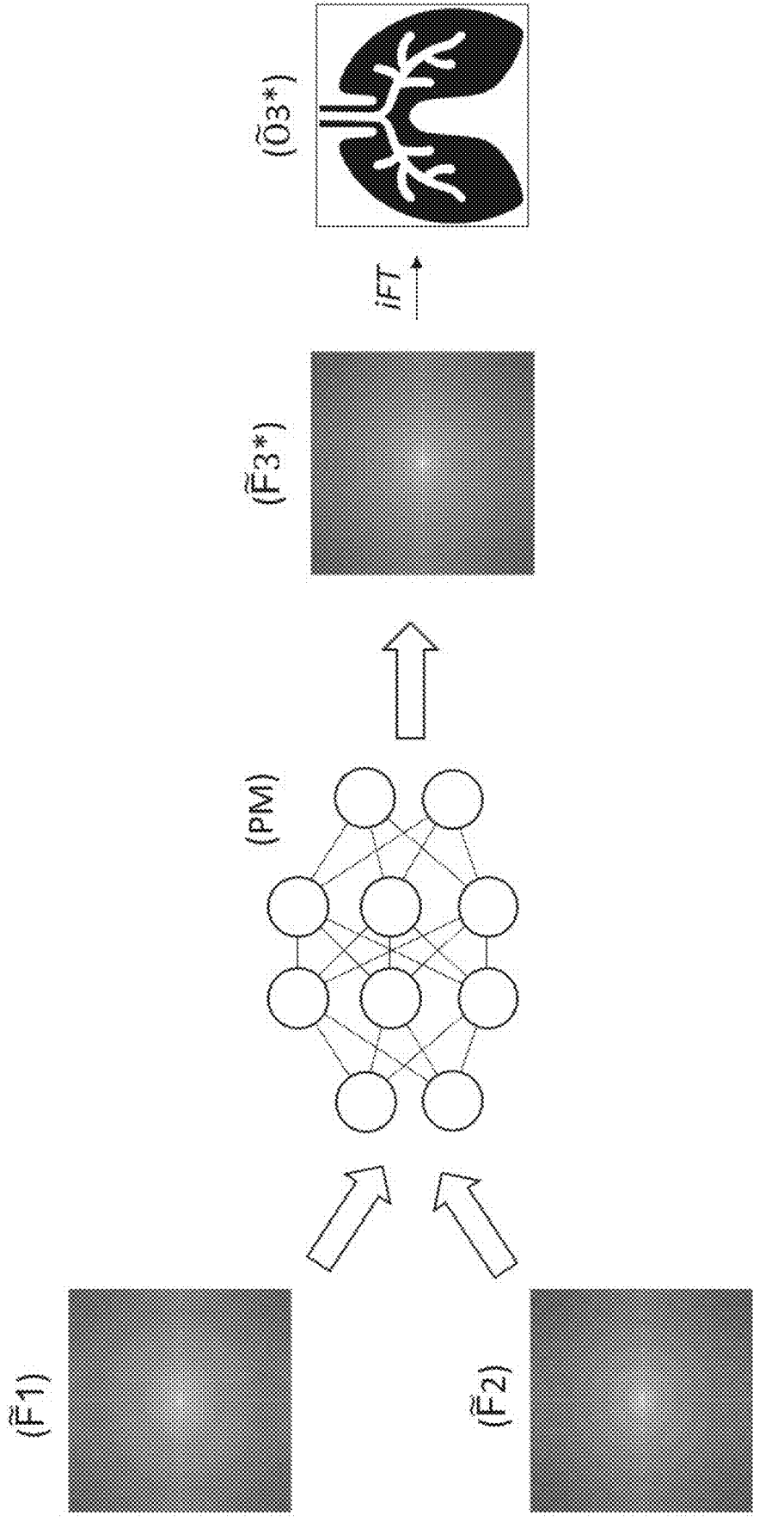
FIG. 4 depicts the use of a trained prediction model, according to some embodiments.

The use of the trained prediction model for prediction is depicted exemplarily and schematically in FIG. 4. FIG. 4 shows the prediction model (PM) trained in FIG. 2. The prediction model is used to predict, on the basis of at least one first representation of the examination region of an examination object in frequency space and at least one second representation of the examination region of the examination object in frequency space, at least one third representation of the examination region of the examination object in frequency space, said representations representing the examination region after the administration of different amounts of contrast agent.

In the present example, a first representation ($\tilde{F}1$) and a second representation ($\tilde{F}2$) of the examination region in frequency space are input into the prediction model and the prediction model generates (calculates) a third representation ($\tilde{F}3^*$). The tilde ($\sim$) signals that the representations are representations of a new examination object, of which usually no representations are present that have been used in the training method for the training of the prediction model. The asterisk (*) signals that the representation ($\tilde{F}3^*$) is a predicted representation. The representation ($\tilde{F}3^*$) of the examination region in frequency space can, for example, be transformed by means of inverse Fourier transform iFT into a representation ($\tilde{O}3^*$) of the examination region in real space.

FIG. 5 shows exemplarily and schematically in the form of a flow chart a preferred embodiment of the method according to the invention for predicting a representation of an examination region of an examination object.

The method (200) comprises the following steps:

(210) receiving a first representation of an examination region of an examination object in frequency space, wherein the first representation represents the examination region without contrast agent or after administration of a first amount of contrast agent, (220) receiving a second representation of the examination region of the examination object in frequency space, wherein the second representation represents the examination region after an administration of a second amount of contrast agent, (230) feeding the first representation and the second representation to a machine learning model, (240) receiving from the machine learning model a third representation of the examination region in frequency space, wherein the third representation represents the examination region after administration of a third amount of contrast agent, (250) generating a representation of the examination region in a real-space depiction on the basis of the third representation, and (260) outputting and/or storing the representation of the examination region in the real-space depiction.

As already described, the representations of the examination region that are used for training, validation, and prediction are representations of the examination region in frequency space (also referred to as spatial frequency space or Fourier space or frequency domain or Fourier representation).

In magnetic resonance imaging, the raw data usually arise as so-called k-space data owing to the above-described measurement method. Said k-space data are a depiction of an examination region in a frequency space, i.e., such k-space data can be used for training, validation and prediction. If representations in real space are present, such representations in real space can, for example, be converted (transformed) by Fourier transform into a representation in frequency space; conversely: representations in frequency space can, for example, be converted (transformed) by inverse Fourier transform into a representation in real space.

Thus, if a radiological image of an examination region is present in the form of a two-dimensional image in real space, this representation of the examination region can be converted by a 2D Fourier transform into a two-dimensional representation of the examination region in frequency space.

A three-dimensional image (volume depiction) of an examination region can be treated as a stack of two-dimensional images. Furthermore, it is conceivable that the three-dimensional image is converted using a 3D Fourier transform into a three-dimensional representation of the examination region in frequency space.

The use of representations of the examination region in frequency space that is according to the invention has various advantages over the use of representations of the examination region in real space.

For example, co-registration of the individual representations is less critical in frequency space than in real space. "Co-registration" (also called "image registration" in the prior art) is an important process in digital image processing and serves to bring two or more images of the same scene, or at least similar scenes, in harmony with one another in the best possible way. One of the images is defined as the reference image and the others are called object images. In order to optimally match these with the reference image, a compensating transformation is calculated. The images to be registered differ from one another because they were acquired from different positions, at different time points and/or with different sensors.

In the case of the present invention, the individual representations were generated at different time points; secondly, they differ with respect to the content of contrast agent in the examination region and/or with respect to the contrast agent used.

The use of representations of the examination region in frequency space has, then, the advantage over the use of representations of the examination region in real space that the training, validation and prediction methods are more tolerant with respect to errors in image registration. In other words: if representations in frequency space are not superimposed with accuracy, this has less influence than if representations in real space are not superimposed with pixel/voxel-accuracy. This is due to the properties of the Fourier transform: as already described, the contrast information of Fourier-transformed images is always mapped in the vicinity of the origin of the Fourier space. Turns or rotations in image space (real space) lead to image information (e.g., a visible structure) being localized in a different region of the image after the transformation. However, in Fourier space, these transformations do not change the region in which the contrast information relevant to the present invention is encoded.

A further advantage of the use of representation in frequency space is that contrast information, which is important for training and for prediction, can be separated from detail information (fine structures). It is thus possible to concentrate, in the case of training, on the information to be learnt by the prediction model and to also concentrate, in the case of prediction, on the information to be predicted by the prediction model: contrast information.

Whereas contrast information in a representation of an examination region in real space is usually distributed over the entire representation (each pixel/voxel intrinsically bears information about contrast), the contrast information in a representation of an examination region in frequency space is encoded in and around the center of the frequency space. In other words, the low frequencies in a representation in frequency space are responsible for the contrast, whereas the high frequencies contain information about fine structures.

It is thus possible to separate the contrast information, to limit training and prediction to the contrast information, and to re-introduce information about the fine structures after training/after prediction.

To this end, a region can be specified in the representations of the examination region that are used for training, validation, and prediction.

Specification of the region can, for example, be achieved by a user inputting one or more parameters into the computer system according to the invention and/or making a selection from a list which defines the shape and/or size of the region. However, it is also conceivable that specification is carried out automatically, for example by the computer system according to the invention, which has been appropriately configured to select a predefined region in the representations of the examination region.

The specified region is usually smaller than the frequency space filled by the respective representation but comprises in any case the center of the frequency space.

A region of the representation that comprises the center of the frequency space (also called origin or zero point) contains the contrast information relevant to the method according to the invention. If the specified region is smaller than the frequency space filled by the respective representation, the calculation complexity for the training, the validation, and the subsequent prediction is lowered. Selection of the size of the region can thus have a direct influence on calculation complexity.

It is in principle also possible to specify a region which corresponds to the entire frequency space which is filled by the respective representation; in such a case, there is no reduction to a subregion of the frequency space and the calculation complexity is maximal.

Thus, by specification of a region around the center of the frequency space, the user of the computer system according to the invention can himself decide whether he wants the complete representations of the examination region in frequency space to form the basis of training, validation, and prediction (which means maximal calculation complexity) or whether he would like to reduce calculation complexity by specifying a region smaller than the frequency space filled by the representations. That is, he can directly influence the required calculation complexity through the size of the specified region.

The specified region usually has the same dimension as the frequency space: in the case of a 2D representation in a 2D frequency space, the specified region is usually an area; in the case of a 3D representation in a 3D frequency space, the specified region is usually a volume.

The specified region can in principle have any shape; it can thus, for example, be round and/or angular, concave and/or convex. Preferably, the region is cuboid or cube-shaped in the case of a 3D frequency space in a Cartesian coordinate system and rectangular or square in the case of a 2D frequency space in a Cartesian coordinate system. However, it is also conceivable that the specified region is spherical or circular or has some other shape.

Preferably, the geometric center of the specified region coincides with the center of the frequency space.

The representations used for training, validation, and prediction are reduced to the specified region. The term "reduce" means here that all the parts of a representation that do not lie in the specified region are cut away (discarded) or are covered by a mask. In the case of masking, those regions which lie outside the specified region are covered with a mask, with the result that only the specified region remains uncovered; when covering with a mask, the colour values of the corresponding pixels/voxels can, for example, be set to zero (black).

The representations thus obtained are also referred to as reduced representations in this description.

The reduced representations can be used for training, validation, and prediction.

Thus, if what is to be predicted for an examination object is a third representation of an examination region on the basis of a first and a second representation, the reduced first representation and the reduced second representation can be fed to the prediction model and the prediction model then generates a reduced third representation. In a further step, the detail information which was cut away or covered during reduction can be re-introduced to the predicted representation. It is thus possible, for example, to introduce the parts of the first representation that lie outside the specified region to the reduced third representation. It is also conceivable that the parts of the second representation that lie outside the specified region are introduced to the reduced third representation. It is also conceivable that both parts of the first representation that lie outside the specified region and parts of the second representation that lie outside the specified region are introduced to the reduced third representation. In other words, the third representation is supplemented by parts of the first and/or the second representation that were cut away/covered with a mask during reduction. The result is a supplemented third representation. From the supplemented third representation, it is then possible to obtain a real-space depiction by a transform (e.g., an inverse Fourier transform).

The resultant signal strengths for various position coordinates can be converted into grey scale values or colour values in a further step in order to have available a digital image in a common image format (e.g., DICOM).

The representation of the examination region in the real-space depiction can be displayed on a screen, output on a printer, and/or stored in a data storage medium.

The approached described will be more particularly elucidated below with reference to FIG. 6 and FIG. 7.

Figure 6:
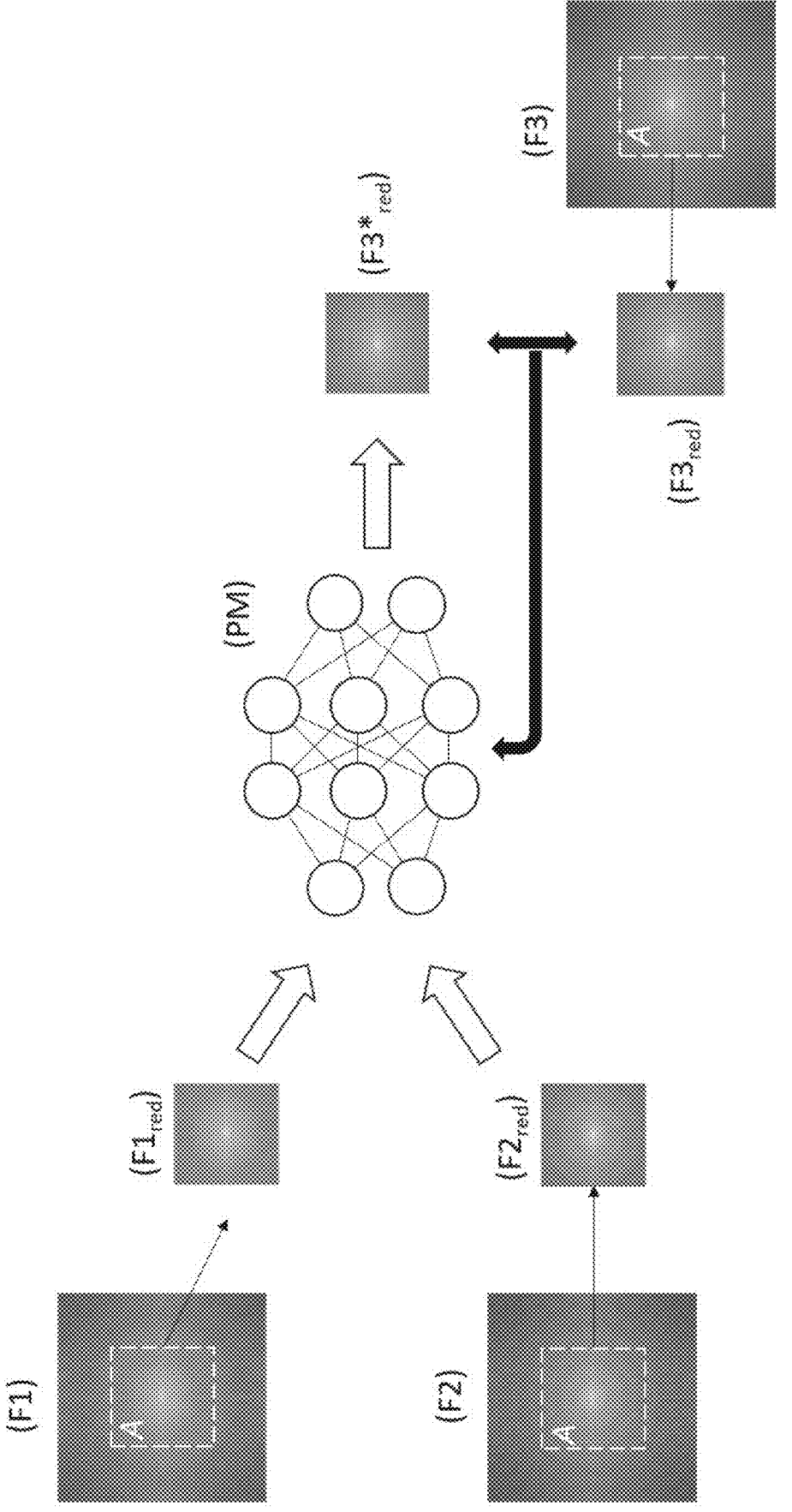
FIG. 6 shows a step in the training of a prediction model, according to some embodiments.

FIG. 6 shows exemplarily and schematically a step in the training of a prediction model according to a preferred embodiment of the present invention.

As in the case of FIG. 2, a first representation (F1), a second representation (F2), and a third representation (F3) of an examination region of an examination object in frequency space are received. In the representations (F1), (F2), and (F3), a region A of the same size and shape is specified in each case. The region A comprises, in each case, the center of the frequency space and has, in the present case, a square shape, with the geometric center of the square coinciding with the center of the frequency space. The representations (F1), (F2), and (F3) are reduced to the respectively specified region A: the result is three reduced representations (F1red), (F2red), and (F3red). The reduced representations are used for the training. The prediction model is trained to predict the reduced representation (F3red) from the reduced representations (F1red) and (F2red). The reduced representations (F1red) and (F2red) are fed to the prediction model (PM) and the prediction model calculates a reduced representation (F3*red) which is to come as close as possible to the reduced representation (F3red).

Figure 7:
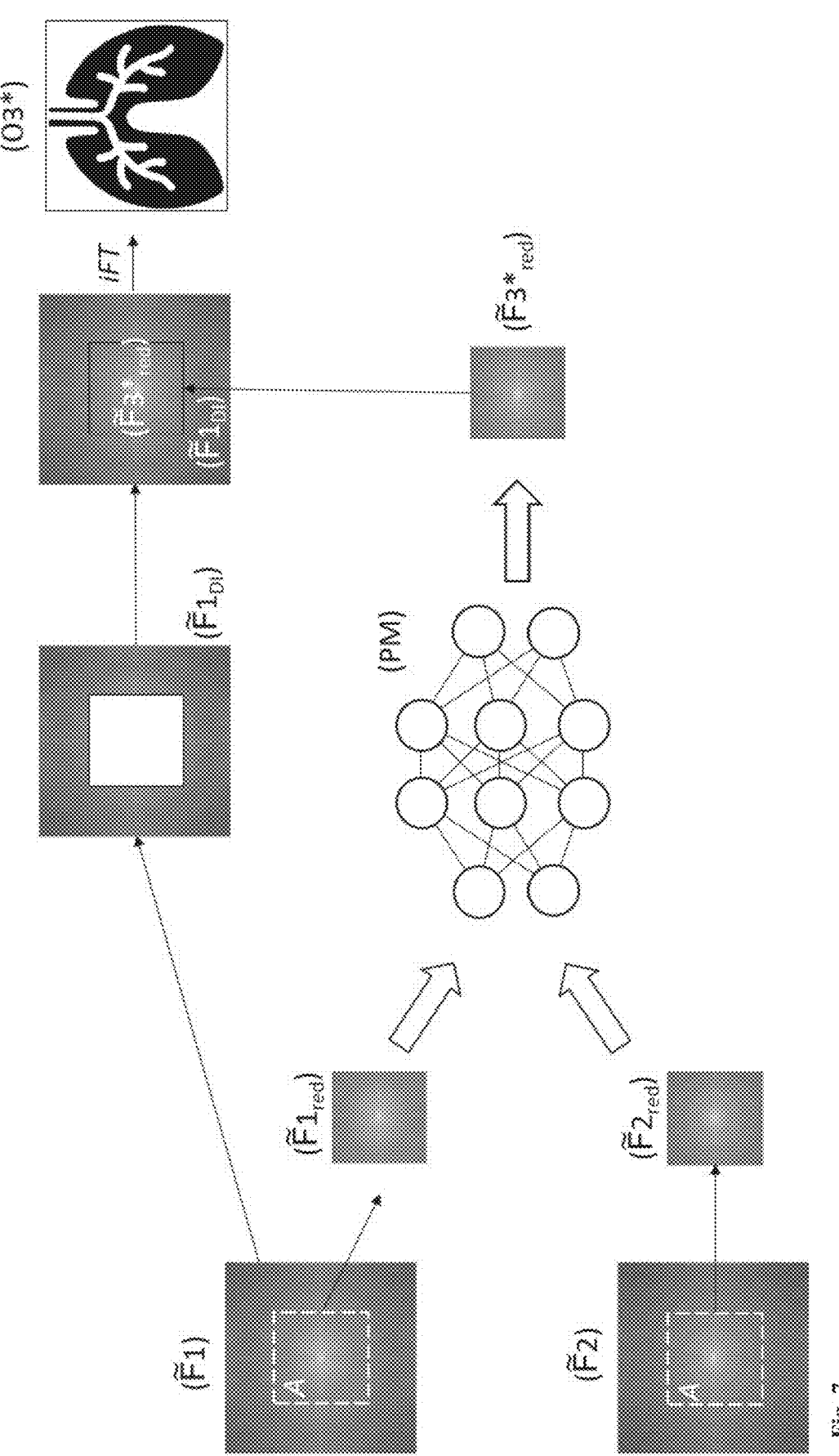
FIG. 7 shows how the prediction model trained in FIG. 6 can be used for prediction, according to some embodiments.

FIG. 7 shows exemplarily and schematically how the prediction model trained in FIG. 6 can be used for prediction.

In the present example, a first representation (F̃1) and a second representation (F̃2) of the examination region in frequency space are received and respectively reduced to a specified region A. The result is two reduced representations ($\tilde{F}$1red) and ($\tilde{F}$2red). The reduced first representation ($\tilde{F}$1red) and the reduced second representation ($\tilde{F}$2red) are fed to the trained prediction model (PM). The trained prediction model (PM) calculates a reduced third representation ($\tilde{F}$3red*) from the reduced representations (Plied) and ($\tilde{F}$2red). In a further step, the reduced third representation ($\tilde{F}$3red*) is supplemented by that region of the received first representation ($\tilde{F}$1) that was discarded during reduction of the received first representation ($\tilde{F}$1). In other words: what are added to the reduced third representation ($\tilde{F}$3red*) are those parts of the received first representation ($\tilde{F}$1) that lie outside (not inside) the specified region. As described, instead of or in addition to parts of the received first representation ($\tilde{F}$1), it is also possible to add parts of the received second representation ($\tilde{F}$2) to the reduced third representation ($\tilde{F}$3red*).

From the supplemented representation ($\tilde{F}$3red*)+($\tilde{F}$1DI), it is possible to generate by inverse Fourier transform a representation of the examination region in real space ($\tilde{O}$3*).

It should be noted that other methods can also be used for transformation of a frequency-space depiction into a real-space depiction, such as, for example, iterative reconstruction methods.

FIG. 8 shows schematically in the form of a flow chart a preferred embodiment for the method according to the invention for training a machine learning model.

The method (300) comprises the steps of:
(310) receiving a training data set, wherein the training data set comprises, for each examination object of a multiplicity of examination objects, i) a first reference representation of an examination region of the examination object in frequency space, ii) a second reference representation of the examination region of the examination object in frequency space and iii) a third reference representation of the examination region of the examination object in frequency space, wherein the first reference representation represents the examination region after administration of a first amount of contrast agent, wherein the first amount can also be zero, wherein the second reference representation represents the examination region after an administration of a second amount of contrast agent, wherein the third reference representation represents the examination region after administration of a third amount of contrast agent,
(320) specifying a region in the reference representations, wherein the specified region comprises the center of the frequency space,
(330) reducing the representations to the specified region, wherein a reduced first reference representation, a reduced second reference representation and a reduced third reference representation are obtained for each examination object,
(340) for each examination object: feeding the reduced first reference representation and the reduced second reference representation to the machine learning model, wherein the machine learning model is trained to generate a reduced representation of the examination region in frequency space after administration of the third amount of contrast agent on the basis of the reduced first reference representation and the reduced second reference representation, wherein the training comprises the minimization of a loss function, wherein the loss function quantifies deviations of the generated reduced representation of the examination region from the reduced third reference representation, and
(350) outputting and/or storing the trained model and/or supplying the trained model to a method for predicting a representation of the examination region of a new examination object.

FIG. 9 shows schematically in the form of a flow chart a preferred embodiment for the method according to the invention for predicting a representation of an examination region of an examination object.

The method (400) comprises the steps of:
(410) receiving a first representation of an examination region of an examination object in frequency space, wherein the first representation represents the examination region without contrast agent or after administration of a first amount of contrast agent,
(420) receiving a second representation of the examination region of the examination object in frequency space, wherein the second representation represents the examination region after an administration of a second amount of contrast agent,
(430) specifying a region in the first representation and in the second representation, wherein the specified region comprises the center of the frequency space,
(440) reducing the first representation and the second representation to the specified region, wherein a reduced first representation and a reduced second representation are obtained,
(450) feeding the reduced first representation and the reduced second representation to a machine learning model,
(460) receiving from the machine learning model a third representation of the examination region in frequency space, wherein the third representation represents the examination region after administration of a third amount of contrast agent,
(470) supplementing the third representation by those parts of the received first and/or the received second representation that do not lie in the specified region,
(480) transforming the supplemented third representation, obtained after the third representation has been supplemented, into a representation of the examination region in a real-space depiction, and
(490) outputting and/or storing the representation of the examination region in the real-space depiction.

FIG. 10 shows schematically in the form of a flow chart a further preferred embodiment for the method according to the invention for predicting a representation of an examination region of an examination object.

The method (500) comprises the steps of:
(510) providing a trained machine learning model, wherein the model has been trained according to the above-described method (100) or (300) to learn the influence of the amount of contrast agent on representations of the examination region in frequency space,
(520) receiving a first representation of the examination region of the examination object in frequency space, wherein the first representation represents the examination region after administration of a first amount of a contrast agent, wherein the first amount can also be zero, and receiving a second representation of the examination region of the examination object in frequency space, wherein the second representation represents the examination region after an administration of a second amount of the contrast agent, (530) optionally: specifying a region in the first representation and in the second representation, wherein the specified region comprises the center of the frequency space, (540) optionally: reducing the first representation and the second representation to the specified region, wherein a reduced first representation and a reduced second representation are obtained, (550) feeding to the machine learning model:
the received first representation and the received second representation, or
if present, the reduced first representation and the reduced second representation, (560) receiving from the machine learning model a third representation of the examination region in frequency space, wherein the third representation represents the examination region after administration of a third amount of the contrast agent, (570) optionally: supplementing the third representation by those parts of the received first and/or the received second representation that do not lie in the specified region, wherein a supplemented third representation is obtained, (580) generating a representation of the examination region in a real-space depiction from:
the third representation, or
if present, the supplemented third representation, and (590) outputting the representation of the examination region in the real-space depiction.

Further embodiments of the present invention include:

1. A computer-implemented method comprising:

receiving a first representation of an examination region of an examination object in frequency space, wherein the first representation represents the examination region without contrast agent or after administration of a first amount of a contrast agent, receiving a second representation of the examination region of the examination object in frequency space, wherein the second representation represents the examination region after an administration of a second amount of contrast agent, specifying a region of the frequency space in the first representation and/or in the second representation, wherein the specified region comprises the center of the frequency space, reducing the first representation and/or the second representation to the specified region, feeding the first representation and second representation obtained after reduction to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of contrast agent, if the frequency space occupied by the third representation is smaller than the frequency space occupied by the received first and/or the received second representation: filling up the frequency space of the third representation with the parts of the received first and/or the received second representation by which the received first and/or the received second representation is/are greater than the third representation, transforming the third representation into a representation of the examination region in a real-space depiction, and outputting the representation of the examination region in the real-space depiction.

2. A computer-implemented method comprising:

receiving a first representation of an examination region of an examination object in frequency space, wherein the first representation represents the examination region without contrast agent or after administration of a first amount of a contrast agent, receiving a second representation of the examination region of the examination object in frequency space, wherein the second representation represents the examination region after an administration of a second amount of contrast agent, specifying a region in the first representation and/or in the second representation, wherein the specified region comprises the center of the frequency space, reducing the first representation and/or the second representation to the specified region, feeding the first representation and second representation obtained after reduction to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of contrast agent, supplementing the third representation by those parts of the received first and/or the received second representation that do not lie in the specified region, transforming the supplemented third representation into a representation of the examination region in a real-space depiction, outputting the representation of the examination region in the real-space depiction, receiving a first representation of an examination region of an examination object in frequency space, wherein the first representation represents the examination region without contrast agent or after administration of a first amount of a contrast agent, receiving a second representation of the examination region of the examination object in frequency space, wherein the second representation represents the examination region after an administration of a second amount of contrast agent, specifying a region in the first representation and/or in the second representation, wherein the specified region comprises the center of the frequency space, reducing the first representation and/or the second representation to the specified region, feeding the first representation and second representation obtained after reduction to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of contrast agent, supplementing the third representation by those parts of the received first and/or the received second representation that do not lie in the specified region, transforming the supplemented third representation into a representation of the examination region in a real-space depiction, and outputting the representation of the examination region in the real-space depiction.

3. A computer-implemented method comprising the steps of:

receiving a first representation of an examination region of an examination object in frequency space, wherein the first representation represents the examination region without contrast agent or after administration of a first amount of a contrast agent, receiving a second representation of the examination region of the examination object in frequency space, wherein the second representation represents the examination region after an administration of a second amount of contrast agent, specifying a region in the first representation and/or in the second representation, wherein the specified region comprises the center of the frequency space, reducing the first representation and/or the second representation to the specified region, feeding the first representation and second representation obtained after reduction to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of contrast agent, supplementing the third representation by those parts of the received first and/or the received second representation that do not lie in the specified region, transforming the supplemented third representation into a representation of the examination region in a real-space depiction, and outputting the representation of the examination region in the real-space depiction.

4. The computer-implemented method of any one of embodiments 1-3, wherein the first amount of contrast agent is greater than or equal to zero, wherein the second amount of contrast agent is greater than the first amount of contrast agent and wherein the third amount of contrast agent is greater than the second amount of contrast agent.

5. The computer-implemented method of any one of embodiments 1-4, wherein the first and the second representation are the result of a radiological examination.

6. The computer-implemented method of any one of embodiments 1-5, wherein the radiological examination is a magnetic resonance imaging examination, a computed tomography examination or an ultrasound examination.

7. The computer-implemented method of any one of embodiments 1-6, wherein the first representation and the second representation are k-space data of a magnetic resonance imaging examination.

8. The computer-implemented method of any one of embodiments 1-7, wherein the first representation and the second representation are Fourier-transformed real-space depictions.

9. The computer-implemented method of any one of embodiments 1-8, further comprising the step of: training the machine learning model, wherein the training comprises:

receiving a training data set, wherein the training data set comprises, for a multiplicity of examination objects, in each case i) a first reference representation of an examination region of the examination object in frequency space, ii) a second reference representation of the examination region of the examination object in frequency space and iii) a third reference representation of the examination region of the examination object in frequency space, wherein the first reference representation represents the examination region after administration of a first amount of a contrast agent, wherein the first amount can also be zero, wherein the second reference representation represents the examination region after an administration of a second amount of the contrast agent, wherein the third reference representation represents the examination region after administration of a third amount of the contrast agent, specifying a region in the reference representations, wherein the specified region comprises the center of the frequency space, reducing the representations to the specified region, wherein a reduced first reference representation, a reduced second reference representation and a reduced third reference representation are obtained for each examination object, and for each examination object: feeding the reduced first reference representation and the reduced second reference representation to the machine learning model, wherein the machine learning model is trained to generate a reduced representation of the examination region in frequency space after administration of the third amount of contrast agent on the basis of the reduced first reference representation and the reduced second reference representation, wherein the training comprises the minimization of a loss function, wherein the loss function quantifies deviations of the generated reduced representation of the examination region from the reduced third reference representation.

10. A computer-implemented method for training a machine learning model, comprising:

receiving a training data set, wherein the training data set comprises, for a multiplicity of examination objects, in each case i) a first reference representation of an examination region of the examination object in frequency space, ii) a second reference representation of the examination region of the examination object in frequency space and iii) a third reference representation of the examination region of the examination object in frequency space, wherein the first reference representation represents the examination region after administration of a first amount of a contrast agent, wherein the first amount can also be zero, wherein the second reference representation represents the examination region after an administration of a second amount of the contrast agent, wherein the third reference representation represents the examination region after administration of a third amount of the contrast agent, specifying a region in the reference representations, wherein the specified region comprises the center of the frequency space, reducing the representations to the specified region, wherein a reduced first reference representation, a reduced second reference representation and a reduced third reference representation are obtained for each examination object, and for each examination object: feeding the reduced first reference representation and the reduced second reference representation to the machine learning model, wherein the machine learning model is trained to generate a reduced representation of the examination region in frequency space after administration of the third amount of contrast agent on the basis of the reduced first reference representation and the reduced second reference representation, wherein the training comprises the minimization of a loss function, wherein the loss function quantifies deviations of the generated reduced representation of the examination region from the reduced third reference representation.

11. A computer system comprising:

a receiving unit, a control and calculation unit, and an output unit, wherein the control and calculation unit is configured to prompt the receiving unit to receive at least two representations of an examination region of an examination object, wherein the representations represent the examination region in frequency space, wherein the representations represent the examination region after administration of different amounts of a contrast agent, wherein the control and calculation unit is configured to reduce the received representations to a specified region, wherein the specified region comprises the center of the frequency space, wherein the control and calculation unit is configured to feed the reduced representations to a machine learning model, wherein the machine learning model has been trained on the basis of a training data set to learn the influence of the amount of contrast agent on the representation of the examination region in frequency space, wherein the control and calculation unit is configured to receive from the machine learning model a predicted representation of the examination region, wherein the predicted representation represents the examination region in frequency space after administration of a specific amount of contrast agent, wherein the control and calculation unit is configured to supplement the predicted representation by those parts of the one or more received representations that lie outside the specified region, wherein the control and calculation unit is configured to transform the supplemented predicted representation into a representation of the examination region in real space, and wherein the control and calculation unit is configured to prompt the output unit to output the representation of the examination region in real space.

12. A computer system comprising:

a receiving unit, a control and calculation unit, and an output unit, wherein the control and calculation unit is configured to prompt the receiving unit to receive at least two representations of an examination region of an examination object, wherein the representations represent the examination region in frequency space, wherein the representations represent the examination region after administration of different amounts of a contrast agent, wherein the control and calculation unit is configured to reduce the received representations to a specified region, wherein the specified region comprises the center of the frequency space, wherein the control and calculation unit is configured to feed the reduced representations to a machine learning model, wherein the machine learning model has been trained on the basis of a training data set to learn the influence of the amount of contrast agent on the representation of the examination region in frequency space, wherein the control and calculation unit is configured to receive from the machine learning model a predicted representation of the examination region, wherein the predicted representation represents the examination region in frequency space after administration of a specific amount of contrast agent, wherein the control and calculation unit is configured to supplement the predicted representation by those parts of one or more of the received representations that do not lie within the specified region, wherein the control and calculation unit is configured to transform the supplemented predicted representation into a representation of the examination region in real space, and wherein the control and calculation unit is configured to prompt the output unit to output the representation of the examination region in real space.

13. A computer system comprising:

a receiving unit, a control and calculation unit, and an output unit, wherein the control and calculation unit is configured to prompt the receiving unit to receive at least two representations of an examination region of an examination object, wherein the representations represent the examination region in frequency space, wherein the representations represent the examination region after administration of different amounts of a contrast agent, wherein the control and calculation unit is configured to reduce the received representations to a specified region, wherein the specified region comprises the center of the frequency space, wherein the control and calculation unit is configured to feed the reduced representations to a machine learning model, wherein the machine learning model has been trained on the basis of a training data set to learn the influence of the amount of contrast agent on the representation of the examination region in frequency space, wherein the control and calculation unit is configured to receive from the machine learning model a predicted representation of the examination region, wherein the predicted representation represents the examination region in frequency space after administration of a specific amount of contrast agent, wherein the control and calculation unit is configured to supplement the predicted representation by the parts from one or more of the received representations that were discarded during reduction, wherein the control and calculation unit is configured to transform the supplemented predicted representation into a representation of the examination region in real space, and wherein the control and calculation unit is configured to prompt the output unit to output the representation of the examination region in real space.

14. A non-transitory computer readable storage medium storing instructions that, when executed by one or more processors of a computer system, cause the computer system to:

receive a first representation of an examination region of an examination object in frequency space, wherein the first representation represents the examination region without contrast agent or after administration of a first amount of a contrast agent, receive a second representation of the examination region of the examination object in frequency space, wherein the second representation represents the examination region after an administration of a second amount of contrast agent, specify a region of the frequency space in the first representation and/or in the second representation, wherein the specified region comprises the center of the frequency space, reduce the first representation and/or the second representation to the specified region, feed the first representation and second representation obtained after reduction to a machine learning model, wherein the machine learning model has been trained on the basis of a training data set to learn the influence of the amount of contrast agent on the representation of the examination region in frequency space, receive from the machine learning model a third representation of the examination region in frequency space, wherein the third representation represents the examination region after administration of a third amount of contrast agent, if the frequency space occupied by the third representation is smaller than the frequency space occupied by the received first and/or the received second representation: fill up the frequency space of the third representation with the parts of the received first and/or the received second representation by which the received first and/or the received second representation is/are greater than the third representation, transform the third representation into a representation of the examination region in a real-space depiction, and output the representation of the examination region in the real-space depiction.

15. A non-transitory computer readable storage medium storing instructions that, when executed by one or more processors of a computer system, cause the computer system to:

receive a first representation of an examination region of an examination object in frequency space, wherein the first representation represents the examination region without contrast agent or after administration of a first amount of a contrast agent, receiving a second representation of the examination region of the examination object in frequency space, wherein the second representation represents the examination region after an administration of a second amount of contrast agent, specifying a region in the first representation and/or in the second representation, wherein the specified region comprises the center of the frequency space, reducing the first representation and/or the second representation to the specified region, feeding the first representation and second representation obtained after reduction to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of contrast agent, supplementing the third representation by those parts of the received first and/or the received second representation that do not lie within the specified region, transforming the supplemented third representation into a representation of the examination region in a real-space depiction, and outputting the representation of the examination region in the real-space depiction.

16. The use of a contrast agent in a radiological method comprising:

generating a first representation of an examination region of an examination object in frequency space, wherein the first representation represents the examination region without contrast agent or after administration of a first amount of a contrast agent, generating a second representation of the examination region of the examination object in frequency space, wherein the second representation represents the examination region after an administration of a second amount of contrast agent, wherein the second amount differs from the first amount, reducing the first representation and the second representation to a specified region, wherein the specified region comprises the center of the frequency space, feeding the reduced first representation and the reduced second representation to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of contrast agent, wherein the third amount of contrast agent differs from the first amount and from the second amount, filling up the frequency space of the third representation by the parts of the received first and/or the received second representation that were discarded during reduction, transforming the filled third representation into a representation of the examination region in a real-space depiction, and outputting the representation of the examination region in the real-space depiction.

17. The use of a contrast agent in a radiological method comprising:

generating a first representation of an examination region of an examination object in frequency space, wherein the first representation represents the examination region without the contrast agent or after administration of a first amount of the contrast agent, generating a second representation of the examination region of the examination object in frequency space, wherein the second representation represents the examination region after an administration of a second amount of the contrast agent, wherein the second amount differs from the first amount, reducing the first representation and the second representation to a specified region, wherein the specified region comprises the center of the frequency space, feeding the reduced first representation and the reduced second representation to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of the contrast agent, wherein the third amount differs from the first amount and from the second amount, supplementing the third representation by those parts of the received first and/or the received second representation that do not lie within the specified region, transforming the supplemented third representation into a representation of the examination region in a real-space depiction, and outputting the representation of the examination region in the real-space depiction.

18. A contrast agent for use in a radiological method, the method comprising:

optionally: administering a first amount of the contrast agent to an examination object, generating a first representation of an examination region of the examination object in frequency space, wherein the first representation represents the examination region without the contrast agent or after administration of the first amount of the contrast agent, administering a second amount of the contrast agent to the examination object, wherein the second amount differs from the first amount, generating a second representation of the examination region of the examination object in frequency space, wherein the second representation represents the examination region after administration of the second amount of the contrast agent, reducing the first representation and the second representation to a specified region, wherein the specified region comprises the center of the frequency space, feeding the reduced first representation and the reduced second representation to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of the contrast agent, wherein the third amount differs from the first amount and from the second amount, supplementing the third representation by those parts of the received first and/or the received second representation that do not lie in the specified region, transforming the supplemented third representation into a representation of the examination region in a real-space depiction, and outputting the representation of the examination region in the real-space depiction.

19. A contrast agent for use in a radiological method, the method comprising:

optionally: administering a first amount of the contrast agent to an examination object, generating a first representation of an examination region of the examination object in frequency space, wherein the first representation represents the examination region without the contrast agent or after administration of the first amount of the contrast agent, administering a second amount of the contrast agent to the examination object, wherein the second amount differs from the first amount, generating a second representation of the examination region of the examination object in frequency space, wherein the second representation represents the examination region after administration of the second amount of the contrast agent, reducing the first representation and the second representation to a specified region, wherein the specified region comprises the center of the frequency space, feeding the reduced first representation and the reduced second representation to a machine learning model, wherein the machine learning model has been trained on the basis of a training data set to learn the influence of the amount of contrast agent on the representation of the examination region in frequency space, receiving from the machine learning model a third representation of the examination region in frequency space, wherein the third representation represents the examination region after administration of a third amount of the contrast agent, wherein the third amount of contrast agent differs from the first amount and from the second amount, supplementing the third representation by those parts of the received first and/or the received second representation that do not lie within the specified region, transforming the supplemented third representation into a representation of the examination region in a real-space depiction, and outputting the representation of the examination region in the real-space depiction.

19. A kit comprising a contrast agent and a computer program according to either of embodiments 14 and 15.

FIG. 11 shows, in schematic form and by way of example, one embodiment of the computer system according to the invention. The computer system (10) comprises a receiving unit (11), a control and calculation unit (12) and an output unit (13).

A "computer system" is an electronic data processing system that processes data by means of programmable computing rules. Such a system usually comprises a control and calculation unit, often also referred to as "computer", said unit comprising a processor for carrying out logical operations and a memory for loading a computer program, and also peripherals.

In computer technology, "peripherals" refers to all devices that are connected to the computer and are used for control of the computer and/or as input and output devices. Examples thereof are monitor (screen), printer, scanner, mouse, keyboard, joystick, drives, camera, microphone, speakers, etc. Internal ports and expansion cards are also regarded as peripherals in computer technology.

Modern computer systems are frequently divided into desktop PCs, portable PCs, laptops, notebooks, netbooks and tablet PCs, and what are called handhelds (for example, smartphones); all of these systems may be used to implement the invention.

Inputs into the computer system (e.g., for control by a user) are achieved via input means such as, for example, a keyboard, a mouse, a microphone, a touch-sensitive display and/or the like. Outputs are achieved via the output unit (13), which can be especially a monitor (screen), a printer and/or a data storage medium.

The computer system (10) according to the invention is configured to predict, from at least two representations of an examination region in frequency space that represent the examination region after administration of different amounts of contrast agent, a representation of the examination region that shows the examination region after the administration of a specific amount of contrast agent, without said specific amount actually having to be administered.

The control and calculation unit (12) serves for control of the receiving unit (11) and the output unit (13), coordination of the data and signal flows between the various units, processing of representations of the examination region, and generation of artificial radiological images. It is conceivable that multiple control and calculation units are present.

The receiving unit (11) serves for receiving representations of an examination region. The representations can, for example, be transmitted from a magnetic resonance imaging system or be transmitted from a computed tomography system or be read from a data storage medium. The magnetic resonance imaging system or the computed tomography system can be a component of the computer system according to the invention. However, it is also conceivable that the computer system according to the invention is a component of a magnetic resonance imaging system or a computed tomography system. Representations can be transmitted via a network connection or a direct connection. Representations can be transmitted via radio communication (WLAN, Bluetooth, mobile communications, and/or the like) and/or wired communication. It is conceivable that multiple receiving units are present. The data storage medium, too, can be a component of the computer system according to the invention or be connected thereto, for example via a network. It is conceivable that multiple data storage media are present.

The representations and possibly further data (such as, for example, information about the examination object, image-acquisition parameters and/or the like) are received by the receiving unit and transmitted to the control and calculation unit.

The control and calculation unit is configured to generate artificial radiological images on the basis of the received data.

Via the output unit (13), the artificial radiological images can be displayed (e.g., on a monitor), be output (e.g., via a printer) and/or be stored in a data storage medium. It is conceivable that multiple output units are present.

As already described, the invention can be used to reduce the amount of contrast agent in a radiological examination. The prediction model can be trained to predict, on the basis of a first representation of an examination region of an examination object that represents the examination region without contrast agent or after administration of a first amount of a contrast agent and on the basis of a second representation of the examination region of the examination object that represents the examination region after an administration of a second amount of the contrast agent, a third representation of the examination region of the examination object, wherein the third representation represents the examination region after administration of a third amount of the contrast agent, wherein the third amount is greater than the first amount and the second amount. Thus, only a first amount (which can also be zero) and a second amount of the contrast agent need to be administered in order to generate radiological images that look as if a larger, third amount of contrast agent had been administered.

The invention can be used to generate artificial radiological images showing an examination region of an examination object after administration of one contrast agent, although a different contrast agent had been administered.

The invention can be used to generate, on the basis of a radiological image of one radiological examination (e.g., magnetic resonance imaging), an artificial radiological image showing the result of a different radiological examination (e.g., the result of computed tomography).

Further applications are conceivable.

The invention claimed is:

1. A method comprising:
administering a first amount of a contrast agent to a patient; receiving, from a magnetic resonance imaging (MRI) machine, a first representation of an examination region of the patient in frequency space, wherein the first representation represents the examination region after administration of the first amount of contrast agent;
administering a second amount of contrast agent to the patient;
receiving, from the MRI machine, a second representation of the patient in frequency space, wherein the second representation represents the examination region after administration of the second amount of contrast agent;
wherein the first representation and the second representation are Fourier-transformed real-space depictions;
feeding at least part of the first representation and at least part of the second representation to a machine learning model,
wherein feeding at least part of the first representation and at least part of the second representation to the machine learning model comprises:
specifying a region in the received first representation and in the received second representation, wherein the specified region comprises a center of the frequency space;
reducing the first representation and the second representation to the specified region to obtain a reduced first representation and a reduced second representation; and
feeding the reduced first representation and the reduced second representation to the machine learning model;
generating, by the machine learning model, a third representation of the examination region in frequency space, wherein the third representation comprises artificial frequency data of the examination region after hypothetical administration of a third amount of contrast agent;
generating an artificial image of the examination region in real space based on the third representation; and displaying the artificial image of the examination region on a display.

2. The method of claim 1, wherein generating the artificial image of the examination region in real space based on the third representation comprises: supplementing the third representation by those parts of the received first and/or the received second representation that do not lie in the specified region to obtain a supplemented third representation; and transforming the supplemented third representation into the artificial image of the examination region in real space.

3. The method of claim 1, wherein the second amount of the contrast agent is not equal to the first amount of the contrast agent, and wherein the third amount of the contrast agent is not equal to the first amount and/or not equal to the second amount.

4. The method of claim 1, wherein the second amount of contrast agent is greater than the first amount of contrast agent, and wherein the third amount of contrast agent is greater than the second amount of contrast agent.

5. The method of claim 1, wherein the third amount of contrast agent comprises a third contrast agent, the second amount of contrast agent comprises a second contrast agent, and the first amount of contrast agent comprises a first contrast agent, wherein the third contrast agent is different from the first contrast agent and/or different from the second contrast agent or wherein the second contrast agent is different from the first contrast agent.

6. The method of claim 1, wherein the first representation and the second representation are k-space data.

7. The method of claim 1, further comprising:

receiving a first real-space representation of the examination region of the patient, wherein the first real-space representation represents the examination region after administration of the first amount of contrast agent;

receiving a second real-space representation of the examination region of the patient, wherein the second real-space representation represents the examination region after administration of the second amount of contrast agent;

generating the first representation of the examination region of the patient object in frequency space from the first real-space representation using a Fourier transform; and generating the second representation of the examination region of the patient object in frequency space from the second real-space representation using Fourier transform.

8. The method of claim 1, further comprising training the machine learning model, wherein the training comprises:

receiving a training data set comprising, for each examination object of a multiplicity of examination objects:

a first reference representation of an examination region of the examination object in frequency space, wherein the first reference representation represents the examination region after administration of the first amount of a contrast agent, a second reference representation of the examination region of the examination object in frequency space, wherein the second reference representation represents the examination region after administration of the second amount of the contrast agent, and a third reference representation of the examination region of the examination object in frequency space, wherein the third reference representation represents the examination region after administration of the third amount of the contrast agent;

specifying a region in the first, second, and third reference representations, wherein the specified region comprises a center of the frequency space;

reducing the first, second, and third reference representations to the specified region to obtain a reduced first reference representation, a reduced second reference representation, and a reduced third reference representation for each examination object of the multiplicity of examination objects of the training data set; and for each examination object of the multiplicity of examination objects of the training data set: feeding the reduced first reference representation and the reduced second reference representation to the machine learning model, wherein the machine learning model is trained to reduce the representation of the examination region in frequency space to obtain a reduced representation of the examination region after administration of the third amount of contrast agent based on the reduced first reference representation and the reduced second reference representation, wherein the training comprises minimizing a loss function, wherein the loss function quantifies deviations of the reduced representation of the examination region from the reduced third reference representation.

* * * * *